United States Patent [19]
Liang et al.

[11] Patent Number: 5,866,570
[45] Date of Patent: Feb. 2, 1999

[54] TREATMENT OF VASCULAR LEAKAGE AND RELATED SYNDROME SUCH AS SEPTIC SHOCK BY ADMINISTRATION OF METALLOPROTEINASE INHIBITORS

[75] Inventors: Chi-Ming Liang, Bethesda; Nancy A. Turner, Germantown, both of Md.; Donald T. Witiak, Madison, Wis.

[73] Assignee: Wisconsin Alumni Research Foundation, Madison, Wis.

[21] Appl. No.: 262,888

[22] Filed: Jun. 21, 1994

Related U.S. Application Data

[63] Continuation-in-part of PCT/US93/04542, May 14, 1993, which is a continuation-in-part of Ser. No. 997,904, Dec. 29, 1992, abandoned, which is a continuation-in-part of Ser. No. 882,855, May 14, 1992, abandoned.

[51] Int. Cl.$^6$ .................................................. A61K 31/535
[52] U.S. Cl. ...................... 514/232.2; 514/250; 514/252; 514/254
[58] Field of Search ............................... 514/1, 72, 232.2, 514/252, 254, 250; 436/74; 424/178.1; 435/4

[56] References Cited

U.S. PATENT DOCUMENTS

| | | |
|---|---|---|
| 4,276,284 | 6/1981 | Brown . |
| 4,950,755 | 8/1990 | Witiak . |
| 5,270,447 | 12/1993 | Liotta . |

FOREIGN PATENT DOCUMENTS

| | | |
|---|---|---|
| 9209556 | 11/1992 | WIPO . |

OTHER PUBLICATIONS

De Clerk et al., J. Biol. Chem. 266:3893–3899, 1991.
Duncan, Biochemical Pharm. 32:3853–3858, 1983.
Dayer, J. Exp. Med 162:2163–2168, 1985.
Welgus, J. Clin Inv. 86:1496, 1502, 1990.
Ceram + Beutler, Immnol. Today 9:28–33, 1988.
Davies, Nature 289:12–13, 1981.
Fritz., Ciba Found Symp 75:351–379, 1979.

*Primary Examiner*—Toni R. Scheiner
*Assistant Examiner*—Nancy A. Johnson
*Attorney, Agent, or Firm*—DeWitt Ross & Stevens S.C.

[57] ABSTRACT

A method for identifying patients at risk of developing vascular leakage syndrome and systemic inflammatory response syndrome (SIRS) such as septic shock by determining the serum levels of metalloproteinase expression, in particular type IV collagenase expression, as well as a method of treating or preventing vascular leakage syndrome and SIRS by the administration of one or more metalloproteinase inhibitors, preferably type IV collagenase inhibitors is taught. Additionally, the therapeutic efficacy of bis (dioxopiperazine) compounds is determined on the basis of collagenase inhibiting activity, and the compounds which inhibit collagenase activity are utilized for the treatment of collagenase related disorders, e.g., vascular leakage syndrome, septic shock, stroke, cardiac disorders, angiogenesis, and arthritis. Finally, a method for preventing or treating toxicity caused by endogenous cytokine expression or cytokine administration or by immunotoxin administration by the administration of one or more metalloproteinase inhibitors, preferably type IV collagenase inhibitors is taught.

2 Claims, 14 Drawing Sheets

1 2 3 4 5 6 7 8 9 10

TREATMENT OF VASCULAR LEAKAGE AND RELATED SYNDROME SUCH AS SEPTIC SHOCK BY ADMINISTRATION OF METALLOPROTEINASE INHIBITORS

This application is a continuation-in-part of International Application No. PCT/US93/04542, filed May 14, 1993, which designated the United States, which is a continuation-in-part of Ser. No. 07/997,904, filed Dec. 29, 1992 and now abandoned; which is a continuation-in-part of Ser. No. 07/882,855, filed May 14, 1992 and now abandoned.

BACKGROUND OF THE INVENTION

This invention relates to a novel method for the treatment of vascular leak and systemic inflammatory response syndrome (SIRS), which conditions include, e.g., sepsis syndrome, septic shock, nonresponsive septic shock, multiple organ dysfunction syndrome, multiple organ failure syndrome and shock resulting from immunologically mediated organ injury, pancreatitis, hemorrhage, ischemia or multitrauma. The invention further relates to a method for identifying patients at risk of developing vascular leakage syndrome and SIRS on the basis of levels of matrix metalloproteinase expression, in particular, expression of collagenases.

The invention further relates to in vitro methods for determining specific compounds which comprise utility in the treatment of vascular leakage syndrome and SIRS, such as septic shock and other metalloproteinase related disorders on the basis of their ability to inhibit the activity of matrix metalloproteinases or to inhibit the expression of matrix metalloproteinases.

Further, the invention provides in vitro methods for screening specific bisdioxopiperazine compounds those of which inhibit matrix metalloproteinases, in particular, type IV collagenases. The invention further relates to methods of using bis(dioxopiperazine) compounds for the treatment of metalloproteinase, in particular collagenase related disorders, such as vascular leakage syndrome and SIRS, particularly septic shock.

It is believed that there are about 400,000 cases of sepsis each year, and 200,000 cases of septic shock, with about 100,000 of such cases resulting in death annually. However, despite the prevalence of these disease conditions, available methods for treatment of sepsis and septic shock are ineffective, at least in part because the precise cause of these disease conditions has been poorly understood.

Sepsis essentially comprises clinical evidence of bacterial infection and symptoms characterized by (i) temperatures in excess of about 101° F., or less than 96° F., (ii) heart rates greater than 90 beats per minute, and (iii) respiratory rates in excess of about 20 breaths per minute. Such symptoms are often followed by hypothermia, nausea, vomiting and diarrhea.

Sepsis syndrome comprises sepsis together with evidence of altered organ perfusion. Such evidence may include one or more of (i) acute changes in mental states, (ii) $Pa_o/Fl_o<280$, (iii) increased lactate levels, and (iv) oliguria (<0.5 ml/Kg for at least one hour).

Septic shock essentially comprises sepsis syndrome together with hypotension which is responsive to intravenous fluids or pharmacological intervention, i.e., systolic blood pressure<90 mm Hg or decrease in mean arterial pressure greater than 40 mm Hg in a hypertensive patient.

Nonresponsive septic shock differs from septic shock in that the hypotension lasts for greater than 1 hour, and is not responsive to intravenously administered fluids or pharmacological intervention.

Septic shock symptoms include tachycardia, hypotension, disseminated intravascular coagulation, and the leakage of plasma proteins into the tissues (vascular leakage syndrome) that may result in peripheral cyanosis, oliguria and edema. Death typically results from renal, respiratory or cardiac failure or a combination thereof.

As yet there is no good way to predict which patients exhibiting infection will develop inflammatory response syndrome (including sepsis) or multiple organ dysfunction syndrome. While some patients with severe infections may not develop sepsis, others, with relatively mild infections and/or symptoms of infection may develop a massive systemic response, i.e., inflammatory response syndrome (including sepsis) or multiple organ dysfunction syndrome.

However, sepsis is the major risk factor in the development of multiple organ failure syndrome. Sequential pulmonary, gastrointestinal, and renal failure may be recognized as early as 12 hours after the beginning of sepsis and septic shock or as late as 7 to 10 days. Because the risk of multiple organ failure syndrome increases with the severity and the duration of septic shock, (although it is not necessarily predictive) it is critically important to restore perfusion as rapidly as possible to avoid late morbidity and reduce the risk of mortality.

The exact pathophysiology of multiple organ failure syndrome is not known. It is hypothesized that injury of the microvascular system, especially the microvascular endothelium, is a factor common to ischemia-reperfusion injury and multiple organ failure syndrome. The microvascular endothelium is thought to be essential in the onset of this syndrome.

Several components of the immunoinflammatory defense system are implicated in the development of microvascular injury: neutrophil (PMN) activation, endothelial activation, complement activation (C5a), platelet-activating factor, arachidonic acid metabolites (LTB4, protacyclin, thromboxane), macrophage activation, the coagulation cascades, and cytokines (e.g., tumor necrosis factor, IL-1, interferon).

Currently available treatments for sepsis and septic shock involve the support of respiration, blood volume replacement, removal of infectious agents by surgery and/or antibiotics, use of vasoactive drugs drugs which increase renal or cardiac functions and glucocorticosteroids.

Although the cause of septic shock is not totally understood, recently various theories have been advanced as to the putative pathway for the induction and development of septic shock. It has been hypothesized that bacterial infection (bacteremia) results in the production of substances, in particular lipopolysaccharides (endotoxins) which induce the formation of cytokines, e.g., IL-1, TNF, PGES and other inflammatory mediators, which in turn result in the production of substances including, e.g., collagenases, nitric oxide and coagulation factors, which increase prior to the onset of vascular leakage syndrome and septic shock.

Currently known and proposed methods of treating septic shock have essentially attempted to kill the bacteria causing the infection, to reduce serum endotoxin levels to inhibit IL-1, TNF, PGES and other inflammatory mediators, or to inhibit nitric oxide or coagulation factors. However, none of the currently available or proposed treatments treats vascular leakage syndrome. This is despite the fact that vascular leakage syndrome, essentially the leakage of plasma proteins from blood vessels into the surrounding tissues, is related to the occurrence of the following symptoms: peripheral cyanosis, oliguria, edema and end-organ failure which may occur during the advanced stages of sepsis and may result in the death of the patient. Thus, a method for treatment of vascular leakage syndrome would be highly beneficial.

As discussed supra, it has been observed that matrix metalloproteinase levels, in particular collagenases such as type IV collagenases increase during sepsis and septic shock. Type IV collagenase enzymes are involved in the breakdown of type IV collagen, a major component of basement membrane, which accounts for about 20–70% of their total mass and forms a supramolecular network which maintains the integrity and rigidity of the basement membrane. Thus, disruption of the collagen IV network is believed to be a critical step in basement membrane degradation. Unlike other basement membrane components, collagen IV is highly resistant to proteolytic degradation by ubiquitous serine proteases but is susceptible to the action to specific metalloproteinases, in particular, the type IV collagenases.

Type IV collagenases are members of a large family of enzymes which include interstitial collagenases, stromelysin, and PUMP-1, which degrade extracellular matrix and basement membrane components. These enzymes all contain a zinc ion which is essential for proteolytic activity, and are secreted in a latent form (zymogen or proenzyme) requiring activation for proteolytic activity, (believed to be affected by plasmin) and are inhibited by a class of naturally occurring inhibitors known as tissue inhibitors of metalloproteinases (TIMP's).

Both normal and tumor cells produce two different but closely related metalloproteinases (MMP's) with type IV collagenase activity, namely, a 72 KD and a 92 KD enzyme respectively known in the literature as MMP-2 and MMP-9 which may be activated by p-AMPA in vitro and activated by plasmin in vivo. It is also known that cells produce natural inhibitors of these enzymes, e.g., TIMP-1 and TIMP-2. The active and inactive forms and substrates for these enzymes are set forth in Table I:

TABLE 1

NOMENCLATURE AND NATURAL SUBSTRATES OF TYPE IV COLLAGENASES

| ENZYME NAMES | MOLECULAR MASS | SUBSTRATES |
| --- | --- | --- |
| MMP-2 proenzyme | 72 KD secreted | gelatin |
| MMP-2 enzyme | 62–64 KD active | gelatin collagens IV, V, VII, X fibronectin, elastin |
| MMP-9 proenzyme | 92 KD secreted | gelatin |
| MMP-9 enzyme | 84 KD active | gelatin collagens IV, V |

The complete amino acid structure has been elucidated for MMP-2 and MMP-9 as well as their inactive prepro and pro-forms, and may be found in U.S. Pat. No. 4,992,537 to Goldberg et al.

The complete amino acid sequences for the endogenous tissue inhibitors of metalloproteinase, i.e., TIMP-1 and TIMP-2 are also known in the art. (DeClerk et al, *J. Biol. Chem.*, 264, 17445 (1989); Boone et al, *Proc. Natl. Acad. Sci.*, USA 87, 2800 (1990); Docherty et al, *Nature*, 318, 65 (1985); and Carmichael et al, *Proc. Natl. Acad. Sci.*, USA, 83, 2407 (1986)).

The expression of matrix metalloproteinases and collagenases in particular have been studied by numerous research groups. For example, mononuclear phagocytes are known to synthesize and secrete a 57 kilodalton interstitial collagenase (MMP-1), a 60 kilodalton stromelysin (MMP-3), a 72 kilodalton type IV collagenase (MMP-2) and a 92 kilodalton type IV collagenase (MMP-9). (Wegus et al., *J. Clin. Invest*, 86, 1496, (1990)).

Additionally, mononuclear phagocyles are known to produce IL-1 and TNF which induces metalloproteinase gene expression (Dayer et al., *J. Clin. Invest.*, 77, 645 (1986); Dayer et al., *J. Exp. Med.*, 162, 2163 (1985)). Moreover, endotoxin has been disclosed to stimulate the synthesis and secretion of MMP-1, MMP-2, MMP-3 and MMP-4 from mononuclear phagocytes in vitro. (Wegus et al., *J. Clin. Invest*, 86, 1496 (1990)).

It has further been reported that TNF stimulates collagenase and PGE2 expression by human synovial cells (Dayer et al., *J. Exp. Med.*, 162, 2163 (1985)), and that it stimulates the biosynthesis of MMP-9 in cultural human chorionic cells (So et al, *Biol. Reprod.*, 46, 772 (1992)) and MMP-9 in osteosarcoma and fibrosarcoma cell lines (Okada et al, *Biochem. Biophys. Res. Commun.*, 171, 610 (1990)). TNF has further been reported to inhibit collagen gene transcription and collagen synthesis in cultured human fibroblasts (Solis-Herruzo et al., *J. Biol. Chem.*, 263, 841 (1988)).

However, to the best knowledge of the present inventors, there had been no recognition that the level of metalloproteinase expression, and in particular type IV collagenase expression, may be used as a means to predict the onset of vascular leakage syndrome or SIRS, e.g., septic shock. Moreover, there had been no recognition that the inhibition of these enzymes could be used to treat or prevent vascular leakage syndrome or SIRS such as septic shock.

As discussed supra, the invention further relates to the identification of particular bis(dioxopiperazine) compounds which inhibit matrix metalloproteinases, in particular collagenases, and the use thereof to treat collagenase mediated conditions or disorders.

Bis(dioxopiperazine)s and in particular 2,6-dioxopiperazines, are currently used in the treatment of various disease conditions, including, e.g., the treatment of cancer, inhibition of cardiac toxicity attributable to anti-cancer drugs such as doxorubicin, psoriasis, as radiation sensitizers during radiotherapy, as well as being proposed for the treatment of arthritis.

2,6-Dioxopiperazines are imides of open chain di(carboxymethyl)amines. The significance of 2,6-dioxopiperazine heterocyclic chemistry and biology evolved as a consequence of exploitation of ethylenediaminetetraacetic acid (EDTA; 1) pharmacology; cyclized imide derivatives of EDTA and related tetraacids are bis(2,6-dioxopiperazine)s wherein the amino N(4) nitrogens of each ring are connected by a central alkene side chain. Medicinal chemical investigations led to the discovery of these important drugs which possess synergistic antitumor, antimetastastic, and cardioprotective properties. For an exhaustive review of the chemistry and biology of regioisomeric dioxopiperazines, See, Witiak and Wei, In: *Progress In Drug Research*, E. Tucker, Ed. Vol. 35, Birkhauser Verlag Base, Boston, (1991), pp 249–363.

The bis(2,6-dioxopiperazine)s, first synthesized in the late 1950's, were thought to have potential for use as textile leveling agents or as pharmaceuticals, but no clear indication for their use was documented. Later, workers at the Imperial Cancer Research Fund (ICRF) introduced rationales for their use as antineoplastic agents providing the impetus for a world wide interest in exploring bis(2,6-dioxopiperazine)s as anti-cancer drugs. (See e.g., Nair et al, *J. Chem. Ed.,* (1988), 65, 534–538; Creighton, U.S. Pat. No. 3,941,790, Creighton et al., *Biochem. J.* (1969), 114, 58P.)

Whereas many antitumor drugs are chelators of metal ions, EDTA (1) or its methyl (or ethyl) esters fail to demonstrate any significant antitumor activity. Reaction of EDTA, however, with formamide generates a diimide known as ICRF-154 (3) having weak antitumor properties in mice. (See Creighton: *Prog. Antimicrob. Anticancer Chemotherapy,* (1970), 1, 167–169; Creighton et al, *Nature,* (1969), 222, 384–385.

The structure of EDTA and methyl or ethyl esters thereof follows:

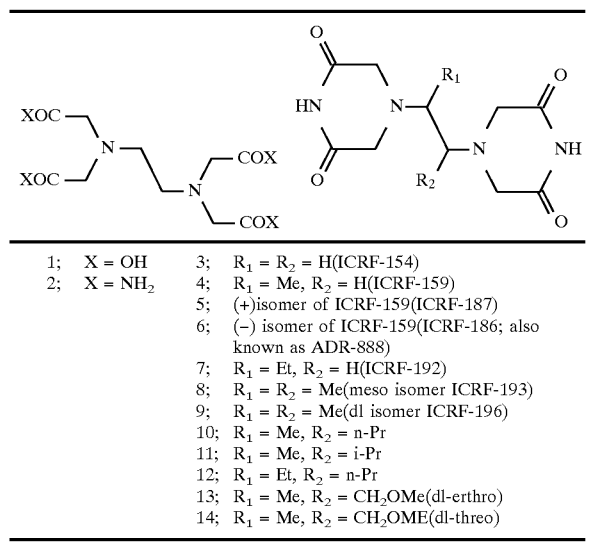

1; X = OH
2; X = $NH_2$
3; $R_1 = R_2$ = H(ICRF-154)
4; $R_1$ = Me, $R_2$ = H(ICRF-159)
5; (+)isomer of ICRF-159(ICRF-187)
6; (−) isomer of ICRF-159(ICRF-186; also known as ADR-888)
7; $R_1$ = Et, $R_2$ = H(ICRF-192)
8; $R_1 = R_2$ = Me(meso isomer ICRF-193)
9; $R_1 = R_2$ = Me(dl isomer ICRF-196)
10; $R_1$ = Me, $R_2$ = n-Pr
11; $R_1$ = Me, $R_2$ = i-Pr
12; $R_1$ = Et, $R_2$ = n-Pr
13; $R_1$ = Me, $R_2$ = $CH_2$OMe(dl-erthro)
14; $R_1$ = Me, $R_2$ = $CH_2$OME(dl-threo)

The related propylene analogue ICRF-159 (razoxane, 4) effects a 93% (5 doses at 30 mg/kg) inhibition of S180 tumors in mice and a 137% (13 doses at 30 mg/kg) increase in survival time in the L1210 leukemia model (Creighton et al, *Nature* (1969), 222, 384–385). The (+) and (−) enantiomers of razoxane are known as ICRF-187 (5) and ICRF-186 (6), respectively. $ID_{50}$ inhibition values for mouse L cell colony formation are for ICRF-154 (3) 7.3 μM, razoxane (4) 3.0 μM, ICRF-192 (7) 720 μM, meso isomer ICRF-193 (8) 0.09 μM, and racemic ICRF-196 (9) 150 μM. Although meso bis(imide) 8 is more potent than razoxane in this assay, its therapeutic index is lower than that of razoxane in vivo. (Creighton et al, *Proc. of the 6th Int. Symp. Med.,* (1978), pp. 281–288, Creighton et al, *Nature,* (1969), pp. 222, 384–385). The calculated ratio of maximum tolerated dose to the dose required for 90% inhibition of S180 tumor growth for ICRF-193=6.7; for razoxane this ratio=9.8.

Inhibition of [$^3$H]thymidine incorporation into monolayers of mouse-embryo fibroblasts reveals $IC_{50}$ values for ICRF-154=2.0 μg/ml, razoxane=0.5 μg/ml, meso ICRF-193=0.035 μg/ml, dl-ICRF-196 (inactive), and a compound having a trans cyclobutanediyl linkage (ICRF-197)—14 g/ml, or a 1,3-propanediyl linkage (ICRF-161) (inactive). (Creighton, *Prog. Antimicrob. Anticancer Chemother.,* (1970), 1, pp. 167–164). Other dl-erythro (10–13) and dl-threo (14) analogues of increased lipophilicity also have considerably decreased activity. (Creighton, *Ger. Offer.,* (1972) 2, pp. 163, 601; Creighton, *Prog. Antimicrob. Anticancer Chemother.,* (1970), 1, pp. 167–169).

Only minor modifications of the bis(imide) system are allowed in order to preserve biological activity. Two intact 2,6-dioxopiperazine moieties are thought to be important for biological activity. Replacement of 2,6-dioxopiperazine rings with other heterocycles, or hydrolysis to produce diamide diacids affords inactive materials, but these hydrolysis products are now thought to have biological significance. Generally, linkages between the two heterocyclic rings having five or fewer carbons produce compounds which are more effective in vitro.

Conformational mobility of the linking group leads to arrangements of dioxopiperazine rings, one or more of which likely is important for various biological activities. Crystal structure analysis of racemic razoxane (4) reveals a cis face-to-face relationship of dioxopiperazine rings; the (+) isomer ICRF-187 has the extended trans conformation with a parallel arrangement of ring planes in the solid state. (Hempel et al, *J. Am. Cancer Soc.* (1982), 104, 3453–3456). These conformations are mimicked by insertion of the 1,2-cyclopropanediyl spacer in place of the 1,2-propanediyl group of razoxane or its optical isomers. (Witiak et al, *J. Med. Chem.* (1978), 21, 1194–1197). The dioxopiperazine rings in these molecules, designated compounds 15 and 16, are held trans in 15 or cis as in 16. Biological properties of trans-15 and cis-16 differ markedly. The cis isomer inhibits, and the trans isomer stimulates development of metastases in two different animal models. (Witiak et al, *J. Med. Chem.,* (1978), 21, pp. 1194–1197; Zwilling et al, *Br. J. Cancer,* (1981), 44, pp. 578–583). Cytostatic activity seems to reside in the cis conformation (see e.g., Witiak et al, *J. Med. Chem.,* (1978), 21, 1194–1197; Zwilling et al, *Br. J. Cancer,* (1981), 44, 578–583), a conformation likely important to biometal chelation mechanisms, but solubility differences between the cis- and trans-1, 2-cyclopropanediyl analogues may also account for differences in observed activities. (Zwilling et al, *Br. J. Cancer,* (1981), 44, 578–583). The structures for these compounds are set forth on the following page:

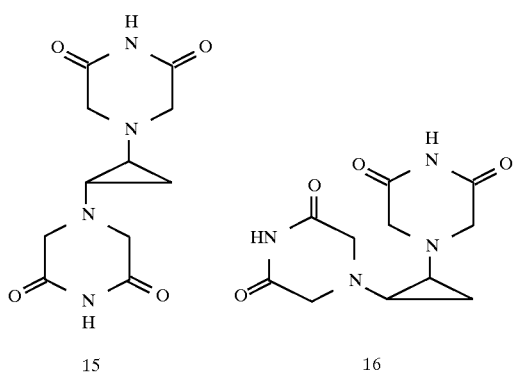

15                     16

The compound cis-16 is prepared from cis-1,2-cyclopropanediyl acid (17) convertible to diamine 18 which undergoes tetra-N-aLkylation to produce intermediate 19. (Witiak et al, *J. Med. Chem.,* (1978), 21, pp. 1194–1197). Trans-15 is similarly synthesized from the trans isomer of 17. (Witiak et al, *J. Med. Chem.,* (1978), 20, 630–635. These compounds are set forth below:

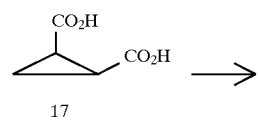

17

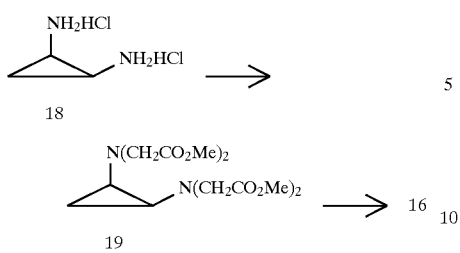

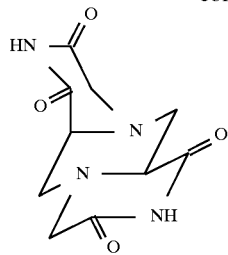

Razoxane has cytoxic activity against V-79A fibroblasts in tissue culture, but trans-15 is inactive. The decrease in activity of trans-15 in this system, and the reported inactivities of 9 and the trans-1,2-cyclobutanediyl bisimide in S180, leukemia L1210 and [$^3$H]-thymidine assays may be related to similarities in their preferred geometries. Cis, not trans geometries, are anticipated to be preferred for most biological activities of bis(dioxopiperazine)s.

Bis(imide)s 20 and 21 are conformationally constrained analogues of ICRF-154 (3) and differ from 3 by two hydrogen atoms in their molecular weight. These geometric isomers are also related to cis-16; removal of the cyclopropyl methylene (CH$_2$ function of 16 with concomitant bond connection between two C(3) carbons of the dioxopiperazine rings provides isomers trans-20 or cis-21. These tricycles are tetraazaperhydrophenanthrenes wherein the dioxopiperazine rings maintain a cisoid relationship. Formal bond disconnection of one carbonyl group from the central piperazine ring of 20 (or 21) and rebonding on the opposite carbon of the central ring provides diastereomers trans-22 and cis-23 belonging to the tetrazaperhydroanthracene series. The dioxopiperazines rings of geometric isomers 22 and 23 have an "extended" rather than "cisoid" geometry. These compounds are depicted below:

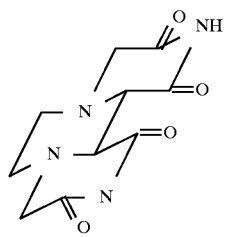

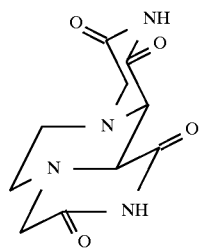

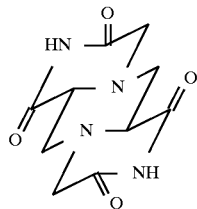

Tricyclic bis(2,6-dioxopiperazine)s 20 and 21 are prepared from pyrazine-2,3-dicarboxiamide (24) convertible to cis-25 (R=Me or Et) via reduction and N-alkylation. (Witiak et al, *J. Med. Chem.*, (1981), 24, pp. 1329–1332). Cyclization of 25 in NaOMe/MeOH produces the trans isomer 20, but in NaOEt/EtOH cis-21 is the exclusive geometric isomer; product geometry is independent of starting esters and likely reflects solubility differences in MeOH vs. EtOH. In MeOH epimerization takes place affording the thermodynamically most stable trans isomer. These structures are set forth on the following page:

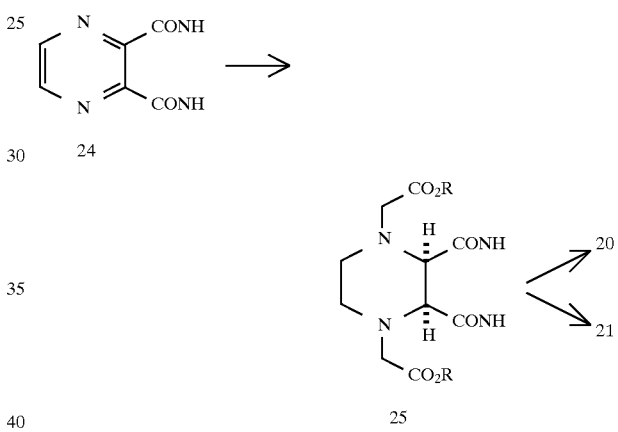

Bis(imide) isomers 22 and 23 may be synthesized following similar reaction sequences using 2,5-dimethylpyrazine (26) as starting material. (Witiak et al, *J. Med. Chem.*, (1985), 28, pp. 1228–1234). Oxidation of methyl groups, ring reduction, and N-alkylation yield respective diastereomers 27 and 28 which are convertible to targets 22 and 23.

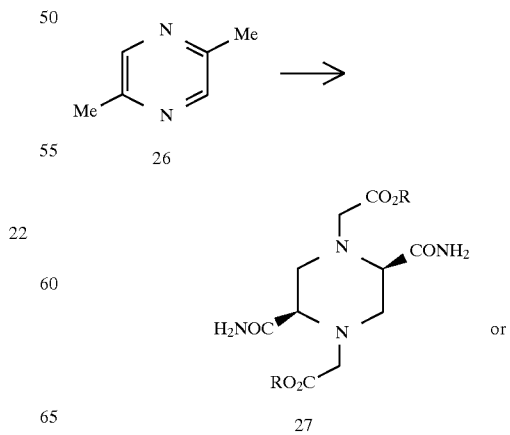

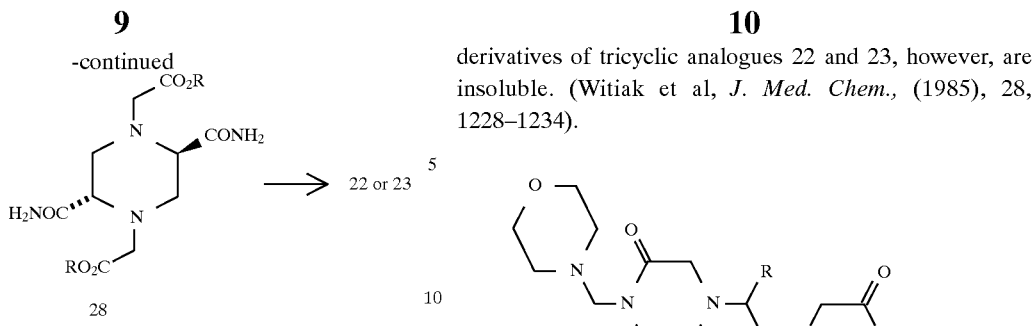

Pretreatment of B16-F10 melanoma cells with trans-20 significantly reduces the metastasis to the lungs of mice at all dose levels (2, 20 and 100 μM), whereas the isomer cis-21 is ineffective in this model. (Witiak et al, *J. Med. Chem.*, (1981), 24, pp. 1321–1332.) Regioisomeric bis(imide)s 22 and 23 have no antimetastatic effects against implanted Lewis lung LL carcinoma in mice, and these data again emphasize the need for a "cisoid" relationship of dioxopiperazine rings. (Witiak et al, *J. Med. Chem.*, (1985), 28, 1228–1234.)

A major problem with bis(2,6-dioxopiperazine) drugs is their poor water solubility. For example, razoxane has a solubility of only 3 mg/ml in water at 25° C. (Ren et al, *Kuexue Tongbao*, (1980), 25, pp. 189–190). Use of cosolvents, complexation, or crystalline modification to overcome low water solubility problems has not been successful. Interestingly, resolution provides enantiomers of razoxane, namely (+) ICRF-187 and (−) ICRF-186, which possess significantly greater water solubility than the racemic material. Additionally, bis(morpholinomethyl) derivatives such as bimolane (29), a derivative of ICRF-154, has increased water solubility. (Ren et al, *Kuexue Tongbao*, (1980), 25, 189–190). Insertion of morpholinomethyl functions into dioxopiperazines does not always afford water soluble materials. The bis(morpholinomethyl) analogue of ICRF-159 (razoxane)(30), also known as probimane, is more water soluble than bimolane (Witiak and Bhat, U.S. Pat. No. 4,871,736 issued Oct. 3, 1989). Morpholinomethyl derivatives of tricyclic analogues 22 and 23, however, are insoluble. (Witiak et al, *J. Med. Chem.*, (1985), 28, 1228–1234).

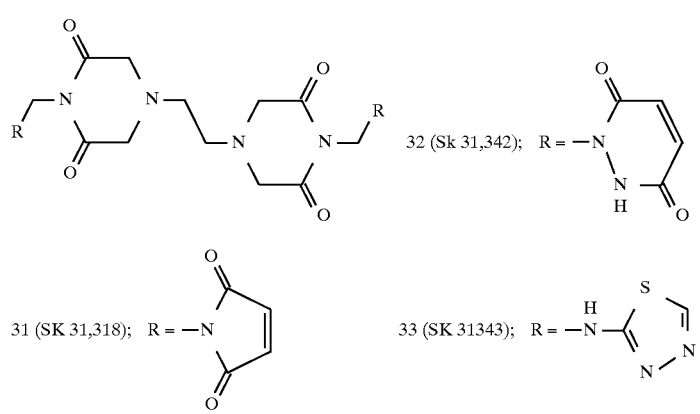

29; R = H
30; R = Me

Other available derivatives (31–33) result from substitution of imide nitrogens with maleimide, a sulfhydro reagent, maleic hydrazide, a plant growth inhibitor having weak antitumor activity, and 2-amino-1,3,4-thiadiazole, a weakly antineoplastic heterocycle. (Ren et al, *Eur. J. Cancer Clin. Oncol.*, (1985), 21, 493–497). When compared for antitumor activity against leukemia L1210, S180, LL carcinoma, and Ridgway osteosarcoma, generally, bimolane and the maleic hydrazide analogue 32 have somewhat better properties. (Ren et al, Id.)

The most potent of many (30, 34–40) bimolane analogues known (Ren et al, 14*th International Congress of Chemotherapy*, Jun. 23–28, 1985, Kyoto, Japan; He et al, *Zhongguo Xaoli Xuebao*, (1988), 9, 369–373; Huang et al, *Zhongguo Xaoli Xuebao*, (1984), 5, 69–71) is probimane (30). Unlike razoxane, probimane may be readily administered parenterally. (Herman et al, *Cancer Chemother. Pharmacol.*, (1987), 19, 277–281).

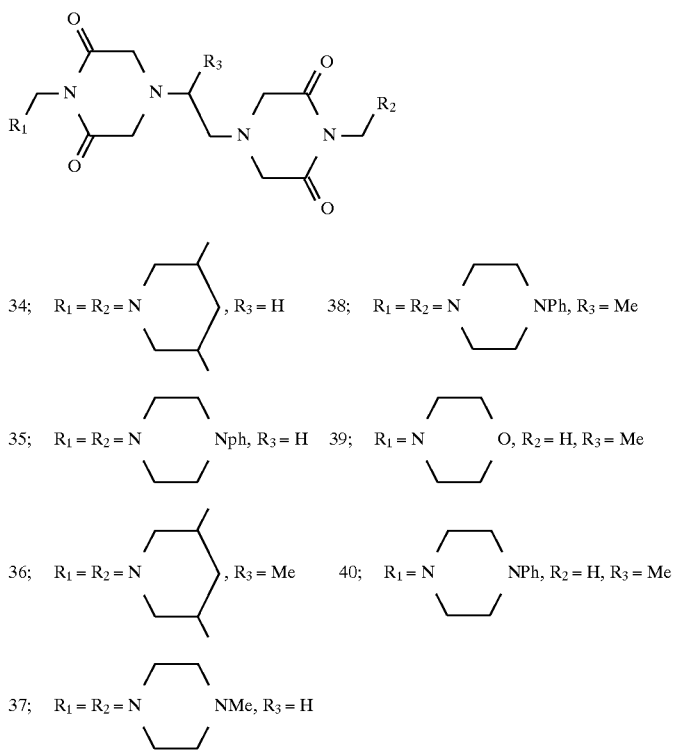

34; $R_1 = R_2 = N\diagup\diagdown$, $R_3 = H$  38; $R_1 = R_2 = N\diagup\diagdown NPh$, $R_3 = Me$ 35; $R_1 = R_2 = N\diagup\diagdown Nph$, $R_3 = H$  39; $R_1 = N\diagup\diagdown O$, $R_2 = H$, $R_3 = Me$ 36; $R_1 = R_2 = N\diagup\diagdown$, $R_3 = Me$  40; $R_1 = N\diagup\diagdown NPh$, $R_2 = H$, $R_3 = Me$ 37; $R_1 = R_2 = N\diagup\diagdown NMe$, $R_3 = H$ Bimolane is unstable, and the antitumor properties exhibited by this compound may reflect chemical hydrolysis or metabolism to ICRF-154 in biological systems. (Camerman et al, Science, (1984), 225, 1165–1166). However, bis(morpholinomethyl) derivatives of tricylic bis(imide)s 18–23 have activities which differ from the parent drugs. This suggests that the bis(morpholinomethyl) species may have intrinsic stereoselective antineoplastic and antimetastatic properties. Perhaps, solubility and transport differences for the various derivatized stereoisomers may be responsible for stereoselective differences in biological activities. (Herman et al, Adv. Pharmacol. Chemother., (1982), 19, 249–290).

Morpholinomethyl derivatives may be easily prepared from the parent bis(dioxopiperazines)s by reaction with morpholine and formaldehyde, and are of interest because of the important clinical results observed for bimolane. Comparative analysis of bis(morpholinomethyl) derivatives of tricycles 20 and 21 with their respective parent bis(imide)s for antitumor effects in mice using a postamputation schedule LL model has shown the bis(morpholinomethyl) derivative of cis-21 to be the most effective inhibitor of metastasis. (Witiak et al, J. Med. Chem., (1985), 28, 1111–1113). However, the bis(morpholinomethyl) derivative of trans-20 also exhibits considerable antimetastatic activity and is more effective than the parent trans bis(imide) 20. The cis dioxopiperazine 21 is a better inhibitor of metastasis than trans-20 in this assay. However, in the B16-F10 model, trans-20 has greater antimetastatic activity than cis-21. (Witiak et al, J. Med. Chem., (1984), 24, 1329–1332). Examination of regioisomeric bis(imides) 22 and 23 and their corresponding bis(morpholinomethyl) derivatives in the LL model reveals that only the morpholinomethyl derivative of cis-23 inhibits metastasis. (Witiak et al, J. Med. Chem., (1985), 28, 1228–1234). Since the parent bis(imide) cis-23 does not exhibit any appreciable antimetastatic effect in this assay, it seems unlikely that the effect of bis(morpholino)-23 is due to its hydrolysis to cis-23. Possibly, but not conclusively, morpholinomethyl derivatives of bis(dioxopiperazine)s possess intrinsic antitumor properties independent of their obvious instability in aqueous systems and their potential as prodrugs.

Many N-acyloxymethyl derivatives (41–51) of ICRF-154 are available. (Cai et al, 14th Intl. Cong. Chemother., Jun. 23, 1985, Kyoto, Japan). Antitumor activities depend upon the nature of the acyl moiety. Compound 50 (MST-16) is the most promising antitumor drug among these derivatives, and is more effective than ICRF-154 and razoxane against Pb388, L1210 and B16 tumors. (Cai et al, Id.). The structure of compounds 41–51 is set forth below:

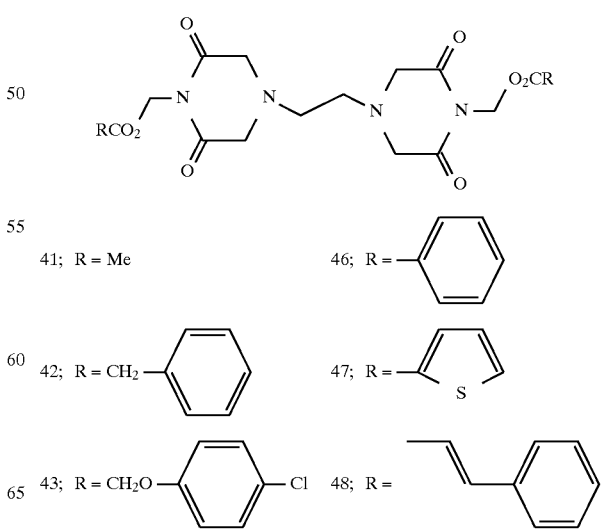

41; R = Me  46; R = —Ph

42; R = CH$_2$—Ph  47; R = —CH$_2$—(thiophene)

43; R = CH$_2$O—Ph—Cl  48; R = —CH=CH—Ph

44; R = CO(CH₂)₂CO₂H  49; R = OCH₃

45; R = CH₂NH₃CF₃COO  50; R = OCH₂CH(CH₃)₂

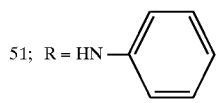

51; R = HN—

Additionally, the synthesis of bis(morpholinomethyl) derivatives of bis(dioxopiperazine)s is disclosed in U.S. Pat. No. 5,130,426, and U.S. Pat. No. 4,950,755, all by Witiak et al, which applications and patents are all incorporated by reference herein.

The synthesis of stereoisomeric tricyclic bis(dioxopiperazines) is also disclosed in U.S. Ser. No. 596,364 filed on Apr. 3, 1984 by Nair et al and U.S. Pat. No. 4,871,736 by Nair et al, which are also incorporated by reference herein. The use of these compounds as antitumor and antimetastatic agents is also taught.

The synthesis of various diastereomeric mono- and di-hydroxylated diamino cyclohexane compounds, in particular, cyclohexane-1,2-di(O—)-4,5-di(N) diastereomers, and the use of such compounds as synthons in the preparation of antitumor platinum complexes is also known as disclosed by Witiak et al, in U.S. Pat. No. 5,206,400, which is also incorporated by reference in its entirety herein.

Recently, Witiak et al, in the "Synthesis and ¹HNMR Conformational Analyses of Diastereomeric 4,4'-(4,5-Dihydroxy-1,2-cyclohexanediyl)bis-2,6-piperazinediones and a Synthetically Related Tricyclic Octahydro-2,2dimethyl-6-oxo-1,3-dioxolo [4,5-g] quinoxaline 5,8-diacetic Acid Ester" submitted to Witiak and Wei, *J. Org. Chem.*, (1991), 56, 5408–5417, and Wei, Yung, Ph.D. Thesis, Ohio State University, 1990, disclosed the preparation of novel diasteriomeric 4,4'-(4,5-dihydroxy-1,2-cyclohexanediyl)bis (2,6-dioxopiperazine)s compounds (88–93) and the synthetically related tricyclic 1,3-dioxolo [4,5-g]quinoxaline ring system compound (86) from their respective (4,5-dihydroxy-1,2cyclohexanediyl)bis (carbamate)s compounds (52–57) via isopropylidene-protected intermediates (58–63). These compounds (88–93) have two hydroxyl groups introduced on the 4 and 5 positions of the cyclohexane-1,2-diyl bis(dioxopiperazine) system were proposed to increase intermolecular hydrogen bonding and to enhance aqueous solubility. The compounds are set forth on the following page:

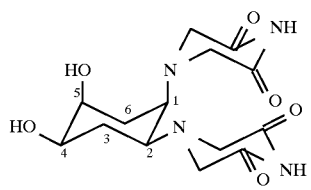

88

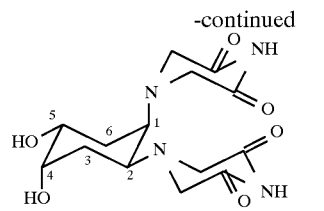

89

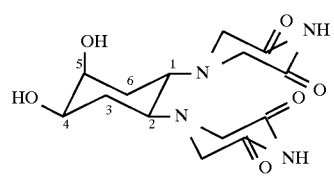

90

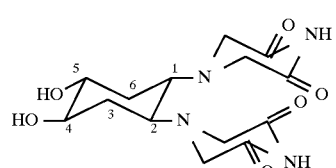

91

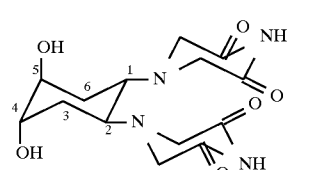

92

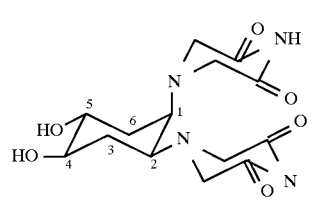

93

The preparation of these compounds is disclosed in Witiak et al, Id. and Wei, Id., which are incorporated by reference in their entirety.

Essentially, known diastereomeric dihydroxy cyclohexanediyl bis(carbamate)s (52–57), were protected as their isopropylidene ketals (58–63), and served as precursors to the intermediate isomeric diamines, five of which (64–68) were convertible to targets (88–93) via tetra (esters) (70–74) and bis(dioxopiperazines) (Witiak et al, Id. and Wei, Id.)[1]. The reaction scheme is set forth on the following page:

[1] The structures for compounds 52–80 may be found in Chart I which is on the following page.

Scheme I

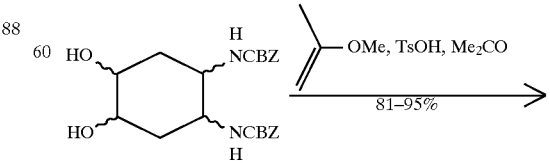

52–57

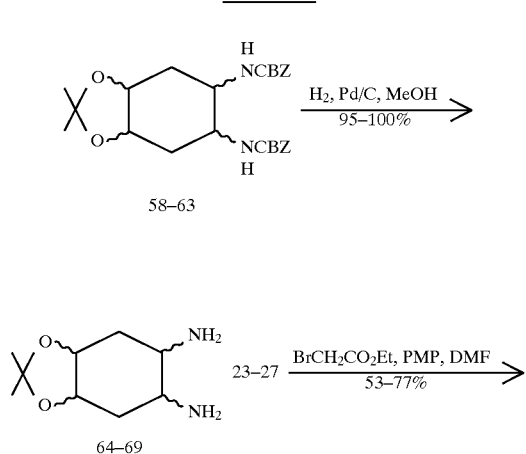
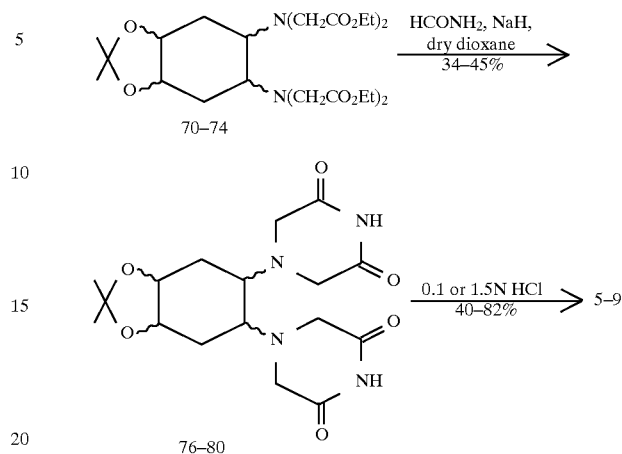
CHART I
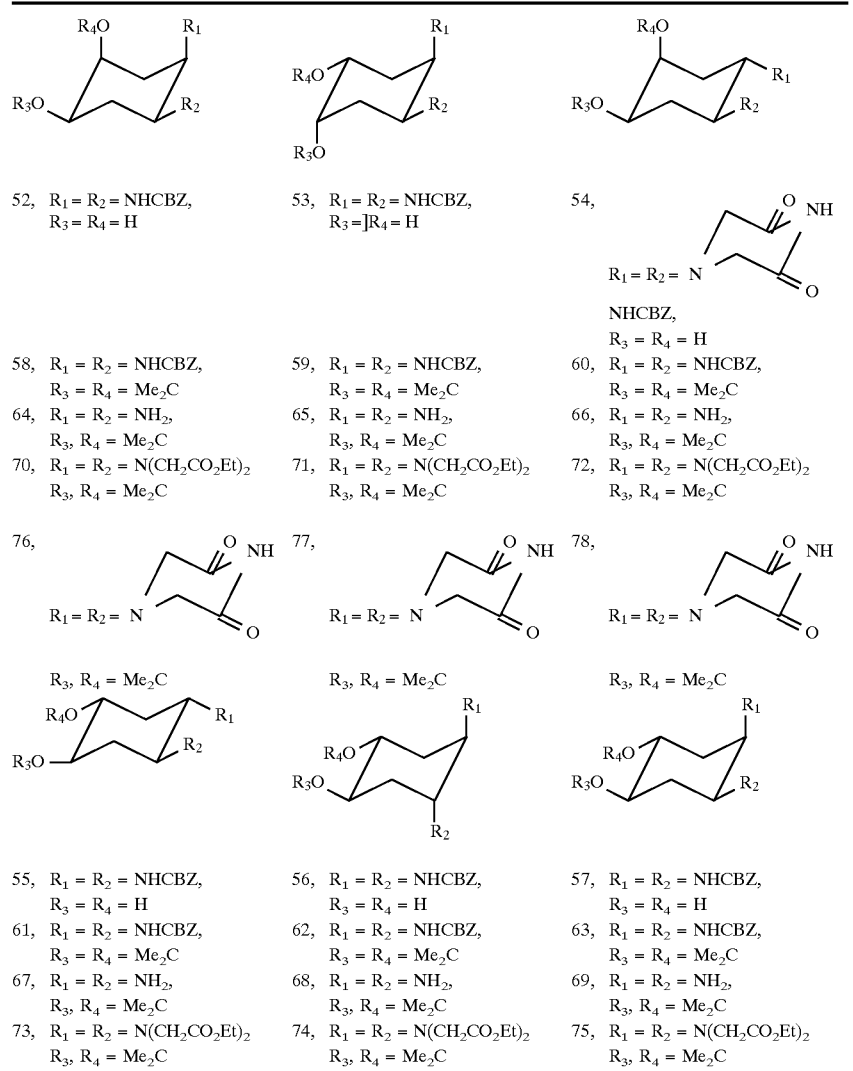

CHART I-continued

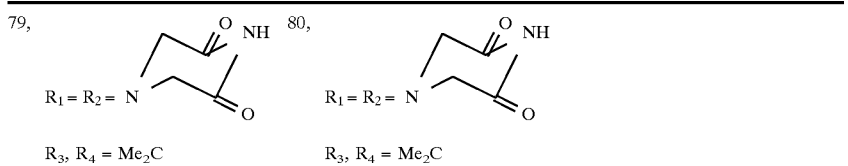

Conversion of diol (52) to the corresponding acetonide (58) using acetone-perchloric acid or trimethylsilyl enol ether was unsuccessful. However, all six protected diastereomers (58–63) were easily prepared employing 2-methoxypropene (2-MP) in TsOH-acetone rather than DMF using the procedures of Fanton et al, *J. Org. Chem.*, (1981), 46, 4007, and Sommer et al, *J. Org. Chem.*, (1971), 36, 82. The individual diastereomer derivatives were obtained in 81–95% yields with relatively minor modifications in the experimental detail such as (a) molar ratios of 2-MP to starting diol, (b) reaction temperatures, and (c) reaction times. The exact details of these modifications may be found in Witiak et al., (Id.).

The diastereomeric diamines (64–69) were obtained in virtually quantitative yield upon catalytic (10% Pd/c) hydrogenation (20 psi; MeOH) of the respective bis(carbamate)s (58–63). However, undesired tricyclic acetone-derived imidazolidines were generated from cis bis(carbamate) diastereomers (58, 59 and 63) during solvent removal under reduced pressure and at room temperature. Imidazolidine formation, however, was precluded when the reagent grade MeOH is replaced by HPLC-grade MeOH which contains<0.001% acetone. All diamines were used without further purification, and five of six compounds, (64–68), underwent tetra(N-alkylation) at room temperature (24 hours) and in 53–77% yield with ethylbromoacetate in DMF containing 1,2,2,6,6-pentamethylpiperazine (PMP). The purification of the tetraesters (70–74) was effected by silica gel chromatography using hexane ethyl acetate (2:1) as an eluant. However, diastereomer (72) was purified using a large diameter-short length column with the addition of 1 drop of triethylamine to each 3 mL of eluant, apparently because of considerable tailing of the diastereomer.

Additionally, since tetra(ester) (71) was obtained from diamine (65) in only 53% yield, Witiak et al developed an alternative synthesis (Scheme II) set forth below:

Scheme II

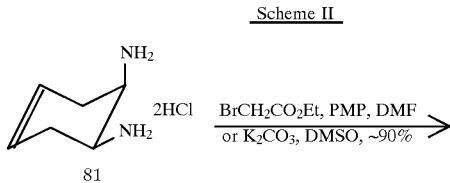

-continued
Scheme II

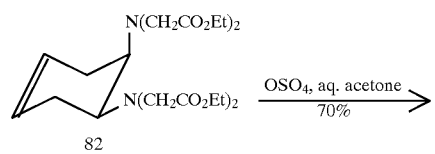

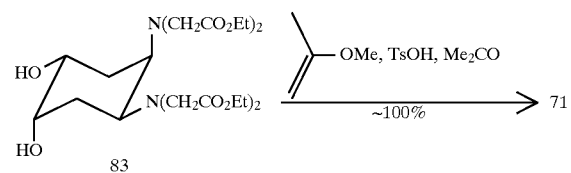

comprising catalytic osmylation of tetra(ester)(82) prepared from the diamine (81). The resulting diol (83), produced in 70% yield, was apparently uncontaminated from the isomer resulting from reaction on the opposite side of the double bond. However, further purification was effected by silica gel chromatography using $CHCl_3$/acetone (3:1) as an eluant. Conversion to acetonitrile (71) was accomplished in approximately 100% yield using 2-MP in TsOH-acetone, confirming the stereochemical assignment for intermediate (83).

The desired tetra(ester) (75) could not be obtained under the experimental conditions used for producing the other five tetra(ester) diastereomers (70–74). Instead, the diamine (69) reacted with three moles of ethyl α-bromoacetate and subsequently underwent intramolecular cyclization to produce either tricyclic trans-anti-cis lactam (86) or the regioisomeric trans-anti-cis lactam (87) likely via intermediates (84) or (85), respectively. This reaction scheme is depicted in Scheme III on the following page:

Scheme III

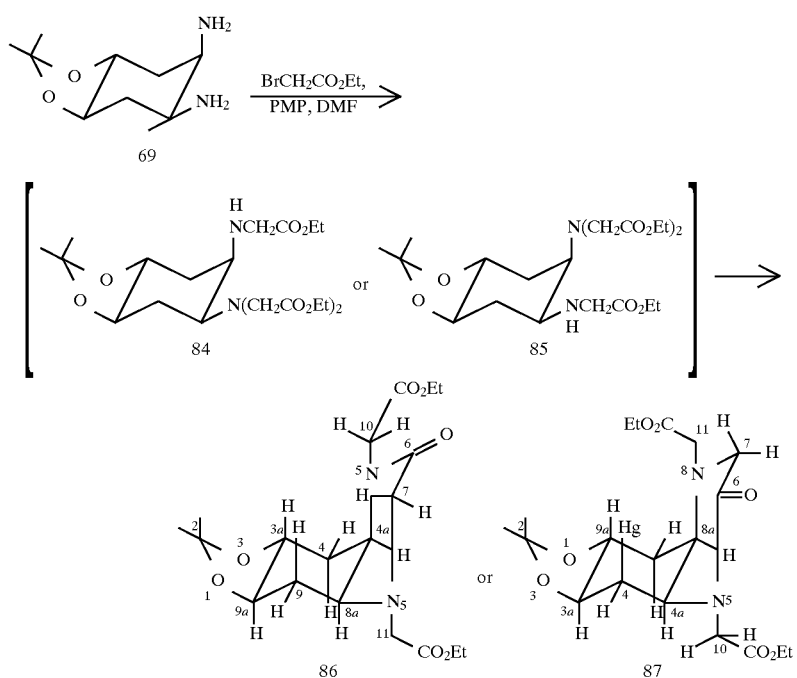

Among the five bis(2,6-dioxopiperazine) diastereomers synthesized, only cis-anti-cis diastereomer (89) exhibits enhanced water solubility (29.3 mg/ml at 25° C.). Wei et al speculate therein that differences in crystal packing, in addition to the relative competition between intra- and intermolecular hydrogen bonding may affect water solubility. It is further hypothesized that the unique 1,4 trans relationship of dioxopiperazine and hydroxyl groups found in this molecule may provide for enhanced water solubility and also reduced melting point because of the loose crystal packing of this conformationally flexible species.

From the above discussion it is clear that many dioxopiperazines are known in the art, and have been utilized as therapeutic agents. However, to date, the exact biological mechanism(s) by which bis(dioxopiperazine)s mediate therapeutic efficacy remains uncertain.

Various groups have studied the biological effects of bis(dioxopiperazine)s in an effort to determine the mode of action for this large class of compounds. These studies have predominantly focused on razoxane, a bis(dioxopiperazine) which is currently used in cancer treatment. Various theories have been advanced as to the biological mechanism by which bis(dioxopiperazine)s mediate therapeutic efficacy. For example, Sharpe et al, *Nature,* (1970), 226, 524, and Hellman et al., *J. Nat'l Cancer Inst.* (1970), 44, 539–543 purport that razoxane mediates a cytostatic effect by inhibiting the transition from $G_2$ to M in the cell cycle. Related to this, Atherton et al, *British J. of Derm.,* (1980), 102, 307 also disclose that razoxane apparently inhibits cell cycle processing during the late pre-mitotic ($G_2$) or early mitotic (M) phase of the cell cycle making this compound potentially applicable in the treatment of psoriasis.

Another possible biological mechanism explaining the therapeutic activity of bis(dioxopiperazine)s involves their "normalization" of tumor cell vasculature. For example, Serve et al., *British Medical Journal,* (1972), 1, 597–601; James et al, *Cancer Research,* (1974), 34, 839–842; and Salsbury et al, *Cancer Research,* (1974), 34, 843–849 disclose that razoxane induces striking changes in the morphology and physiology of tumor vasculature which results in their appearance and behavior resembling that of normal blood cells. It is suggested that these changes may explain the antimetastatic effect of razoxane. This theory finds support, e.g., in Olweny et al, *Cancer Treatment Reports,* (1976), 60(1); 111–113 who disclose the treatment of Kaposi's sarcoma, a highly vascular sarcoma, with razoxane and teach the antimitotic effects and vascular normalizing activity of razoxane.

Another possible explanation for the therapeutic effects of bis(dioxopiperazine)s involves their chelating activity. For example, Herman et al, *Cancer Chemother. Pharmacol.,* (1987), 19, 277–281, summarize that a bis (morpholinomethyl) derivative of razoxane likely inhibits chronic doxorubicin cardiotoxicity because of its ability to chelate iron thereby inhibiting the formation of iron-doxorubicin complexes which result in highly reactive and toxic oxygen-containing free radicals.

Yet another theory explaining the therapeutic activity of bis(dioxopiperazine)s involves their putative inhibition of mammalian DNA topoisomerase II. DNA topoisomerases are the enzymes involved in the conversion of DNA topology which are essential for many genetic processes. Recently, many antitumor agents have been shown to be topoisomerase-targeting drugs. Tanabe et al, *Cancer Research,* (1991), 51, pp. 4903–4908 and Ishida et al., *Cancer Research,* (1991), 51, 4909–4916 disclose that bis (2,6-dioxopiperazine)s inhibit topoisomerase II by preventing etoposide-induced cleavable complex formation and that this inhibition may relate to the abnormal appearance of cells in the $G_2$ and early M phase of the cell cycle.

Still another theory explaining the antitumor activity of razoxane involves its possible effects on basement membrane collagen degradation. For example, Karakiulakis et al, *Meth Find. Exp. Clin. Pharmacol.,* (1989), 11(4), 255–261, hypothesize that razoxane inhibits degradation of intact basement membrane or of type IV collagen. However, inhibition was not proven since an ammonium sulfate enzyme extract obtained from Walker 256 carcinosarcoma was used rather than a pure enzyme. Another group, Boggust et al, *British J. Cancer,* (1978), 38, 329–334 purport that collagen-peptidase activity in HeLa cell extracts and human tumors is inactivated by razoxane and that this inhibition may be involved in the prevention of metastasis. However, this study was also inconclusive since crude HeLa cell extracts were utilized rather than purified enzymes.

Also, Duncan et al, *Biochemical Pharmacol.,* (1983), 32 (24), 3853–3858 teach that razoxane inhibits the production of collagenases and specific tissues inhibitor of metalloproteinase (TIMP) by stimulated articular chondrocyes, and that this may be involved in the therapeutic efficacy of razoxane for treatment of psoriatic arthritis.

Yet another theory explaining the efficacy of bis (dioxopiperazine)s is that they exhibit antitumor activity by mediating a combination of several independent functions, including, e.g., the inhibition of enzymes; cytostatic or cytotoxic action; and immunosuppressive effects. For example, Boggust, *Excerpta Medica,* (1978), 4, 106–112 disclose that the antitumor activity of razoxane may be attributable to a combination of effects which include: (1) effect on growth and metabolism of cancer cells in primary tumors, (2) effect upon enzymes and other factors which regulate tumor cell retention and release, (3) effect on viability of malignant cells within vessels of the circulatory system, (4) effect on enzymes which degrade structural components of the capillary wall and endothelial intercellular cement (basement membrane), (5) release of factors from tumor which regulate capillary growth and formation and (6) effect on growth of capillary endothelial cells stimulated by tumor growth promoters.

Thus, while there exist many theories as to how bis (dioxopiperazine)s mediate therapeutic effects, a conclusive biological mechanism(s) which explains, or is at least predicative as to the therapeutic efficacy of a particular bis (dioxopiperazine) compound, is currently unavailable.

SUMMARY OF THE INVENTION

Metalloproteinase levels, in particular collagenases, and more specifically type IV collagenases, increase prior to vascular leakage syndrome and septic shock. Accordingly, since such enzymes degrade type IV collagen, the major component of basement membrane, it was theorized by the present inventors that the increased expression of these enzymes may be involved in the degradation of basement membrane of blood vessels, which results in the leakage of macromolecules therefrom into surrounding tissues which may result in vascular leakage syndrome and shock.

Thus, the present invention is directed to the treatment of vascular leakage syndrome and SIRS such as septic shock by administering to a patient substances which inhibit metalloproteinases, in particular type IV collagenases, and/ or substances which inhibit the expression of metalloproteinases, in particular type IV collagenases, and more particularly MMP-9 and/or MMP-2. It is theorized by the present inventors that administration of such substances prevents the degradation of basement membrane and blocks the leakage of macromolecules into surrounding tissues thereby preventing or reducing vascular leakage syndrome and SIRS such as septic shock. However, the inventors do not want to restrict themselves to this belief.

The invention further relates to a method for quickly identifying those patients who are at risk for developing vascular leakage syndrome and SIRS. Essentially, this method will entail measuring metalloproteinase expression, in particular type IV collagenase expression, and more particularly MMP-9 or MMP-2 expression and comparing expression levels to normal ranges of expression for these particular enzymes. Those patients exhibiting elevated metalloproteinase levels, especially MMP-9 and MMP-2, will be considered to be at risk for developing vascular leakage syndrome and SIRS related shock. Accordingly, these patients will be treated with metalloproteinase inhibitors, especially collagenase inhibitors and/or compounds which reduce metalloproteinase expression, in particular, the expression of type IV collagenases such as MMP-9 and MMP-2. These assays may be effected using standard diagnostic methods, using specific probes capable of detecting enzyme expression, e.g., antibodies which specifically bind to metalloproteinases such as MMP-9 and MMP-2, or cDNA capable of specifically binding to mRNA's which encode for metalloproteinases, and type IV collagenases, in particular, MMP-9 and MMP-2.

The invention further relates to the use of a specific class of compounds, i.e., bis(dioxopiperazine)s for the treatment of collagenase related disorders. While bis(dioxopiperazine) s, such as razoxane, had previously been theorized to be capable of inhibiting collagenases, the present inventors have provided convincing in vitro evidence that bis (dioxopiperazine)s inhibit collagenases, including, e.g., MMP-9 and MMP-2, and that bis(dioxopiperazine)s which are capable of inhibiting collagenases may be used to treat collagenase related diseases and disorders.

The invention further provides in vitro methods for identifying those bis(dioxopiperazine) compounds which inhibit collagenase which are useful in the treatment of collagenase related diseases and disorders, such as vascular leakage syndrome, septic shock and metastasis, and the use of such compounds for the treatment of collagenase related disorders and metastasis. Collagenase related diseases and disorders include, e.g., rheumatoid arthritis, ulcerated conditions (e.g., caused by burn or infections), periodontal disease and epidermolysis bullosa, stroke, cardiac disorders and angiogenisis.

The invention further relates to a method for treatment of cytokine mediated toxicity caused by endogenous cytokine expression or by the therapeutic administration of cytokines, comprising the administration of one or more substances which inhibit metalloproteinases, in particular type IV collagenases, and more particularly MMP-9 or MMP-2; or which inhibit the expression of metalloproteinases, especially type IV collagenases, and most particularly MMP-9 and MMP-2.

The invention further relates to a method for alleviating the toxic side-effects of immunotoxins by administering to a subject undergoing immunotoxin therapy, one or more substances which inhibit metalloproteinases, in particular type IV collagenases, and more specifically MMP-9 or MMP-2, or substances which inhibit the expression of metalloproteinases, especially type IV collagenases, and most particularly MMP-9 and MMP-2.

DETAILED DESCRIPTION OF THE FIGURES

Figure 1A:
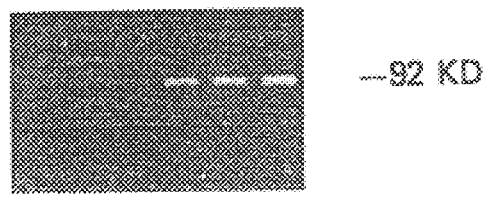

FIG. 1A Gelatin zymogram evaluation of type IV collagenase in the conditioned medium of TNF treated THP-1 cells. The cells were cultured in RPMI 1640 supplemented with 10% FCS, $5 \times 10^{-5}$M 2-ME, and glutamine to a density of $3-5 \times 10^{-5}$ cells/ml. The cells were then washed with RPMI 1640 twice and incubated at a density of $4 \times 10^5$ cells/ml in serum free RPMI 1640 medium supplemented with serial dilutions of rTNF. After 18 h incubation, the conditioned medium was concentrated and its activity was analyzed by gelatin zymogram (5 µl/lane). The conditioned medium of each lane was from the cells pretreated with rTNF for 18 h in the following concentrations: (1) 0 ng/ml; (2) 0.04 ng/ml; (3) 0.2 ng/ml; (4) 1 ng/ml; (5) 5 ng/ml; (6) 25 ng/ml. This is the typical example of these experiments.

Figure 1B:
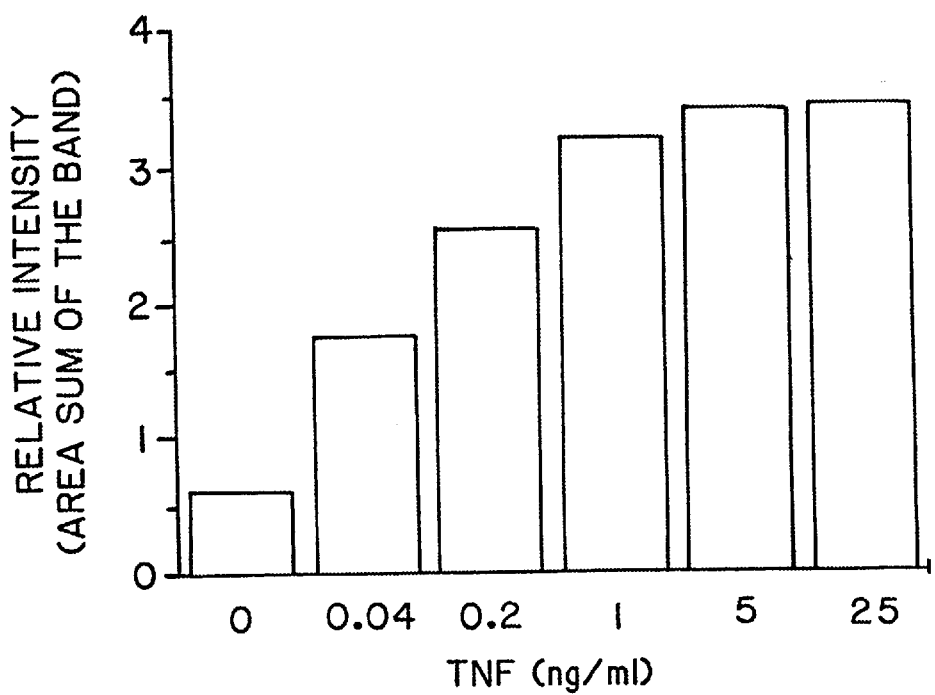

FIG. 1B Quantitation of gelatin zymogram. The amount of gelatin degraded by type IV collagenases was quantitated by measuring the bands of FIG. 1A with an Ultrascan XL enhanced laser densitometry (LKB, Piscataway, N.J.).

Figure 2:
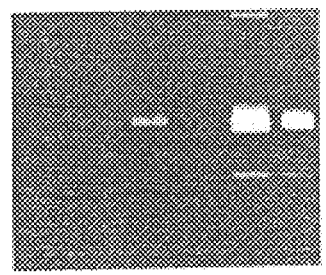

FIG. 2 Gelatin zymogram evaluation of type IV collagenase in the conditioned medium of cytokine treated THP-1 cells. After 24 h incubation, the conditioned medium was concentrated and its activity was analyzed by gelatin zymogram (10 µl/lane). The conditioned medium of each lane was from the cells ($4 \times 10^5$ cells/ml) pretreated with cytokine as follows: (1) none; (2) rIL-4 (25 ng/ml); (3) rIL-6 (25 ng/ml); (4) rIFN-gamma (20 ng/ml); (5) rTNF (50 ng/ml); (6) rIL-1 (20 ng/ml). Similar results were found in two experiments.

Figure 3:
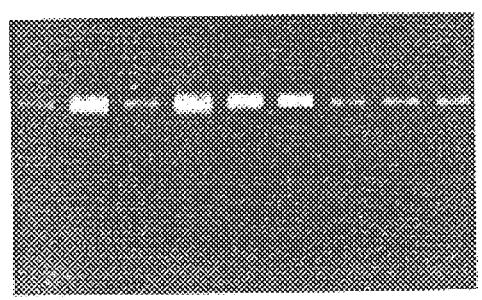

FIG. 3 Influence of anti-TNF and anti-IL-1 antibodies on the effect of TNF and IL-1. The THP-1 ($5 \times 10^5$ cells/ml) were pretreated with TNF or IL-1 in the presence of anti-TNF or anti-IL-1 antibodies. After 24 h incubation, the conditioned medium was concentrated and the collagenase activity in the conditioned medium was analyzed by gelatin zymogram (10 µl/lane). The conditioned medium of each lane was from the cells pretreated with the following: (1) none; (2) rTNF (25 ng/ml); (3) rTNF (25 ng/ml)+anti-TNF antibodies; (4) rTNF (25 ng/ml)+anti-IL-1 antibodies; (5) rIL-1 (25 ng/ml), (6) rIL-1 (25 ng/ml)+anti-IL-1 antibodies; (8) anti-TNF antibodies; (9) anti-IL-1 antibodies. The amounts of the antibodies used were in 2–4 fold excess than required to neutralize the activities of their respective antigens.

Figure 4:
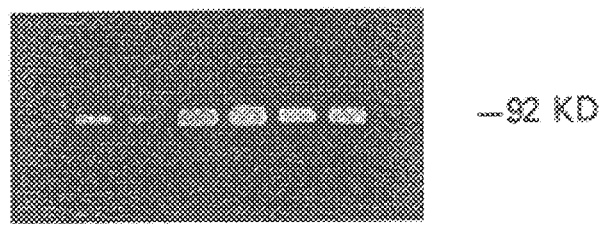

FIG. 4 Effect of anti-IL-2 and anti-TNF antibodies on the activities of IL-6. Gelatin zymogram evaluation of type IV collagenases in the conditioned medium of THP-1 cells pretreated with the following: (1) none; (2) rIL-6 (25 ng/ml); (3) rIL-6 (25 ng/ml) and anti-IL-6 antibodies (200 ng/ml); (4) rTNF (25 ng/ml); (5) rTNF (25 ng/ml)+anti-IL-6 antibodies (200 ng/ml); (6) rIL-1 (25 ng/ml); (7) rIL-1 (25 ng/ml)+anti-IL-6 antibodies (200 ng/ml); (8) rIL-6 (25 ng/ml)+anti-TNF antibodies (10 µg/ml).

Figure 5:
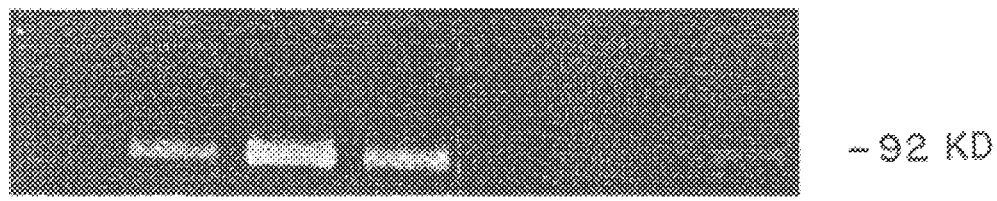

FIG. 5 Gelatin zymogram evaluation of type IV collagenases in the conditioned medium of TNF-treated human primary monocytes. The conditioned medium in each lane was from the cells pretreated with TNF in the presence or absence of anti-TNF antibodies for 18 h in the following concentrations: (1) none; (2) 0.5 ng/ml TNF; (3) 5 ng/ml TNF; (4) 50 ng/ml TNF; (5) 0.5 ng/ml TNF+anti-TNF antibodies (10 µg/ml); (6) 5 ng/ml TNF+anti-TNF antibodies (10 g/ml); (7) 50 ng/ml TNF+anti-TNF antibodies (10 µg/ml).

Figure 6:
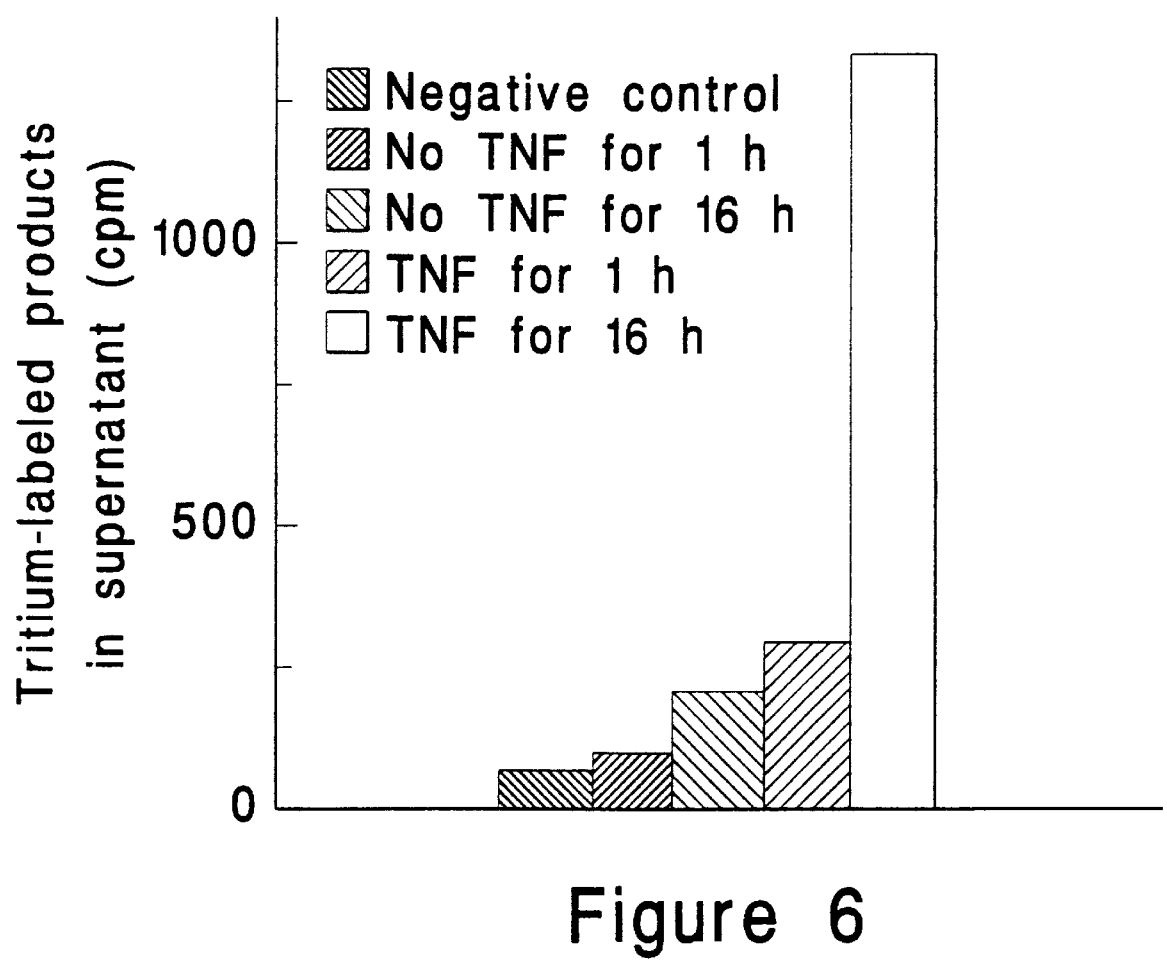

FIG. 6 Enzymatic assay of type IV collagenases in the conditioned medium of human primary monocytes. The elutriated human monocytes were incubated in serum free RPMI 1640 in the presence or absence of rTNF (25 ng/ml) for 1 or 16 h as indicated. After incubation, the supernatant (1 ml) was concentrated by ultrafiltration. The final volume was adjusted with double distilled water to 60 µl and 10 µl was used in each assay. The type IV collagenase activity was assayed by using $^3$H-labeled type IV collagen as a substrate according to the method described by Liotta et al Biochem., (1981), 20, 100. 5000 cpm of $^3$H-labeled type IV collagen was used in each assy. Without being degraded by type IV collagenase, the majority of $^3$H-labeled type IV collagen was precipitated in tannic acid/trichloroacetic acid solution and therefore not detectable in the supernatant (Liotta et al, Biochem., (1981), 20, 100). The increase in the amount of $^3$H-labeled degraded products indicates the presence of more type IV collagenase in the conditioned medium.

Figure 7:
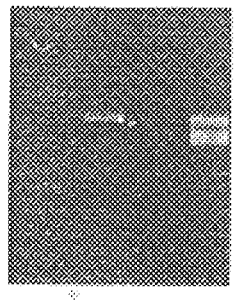

FIG. 7 Influence of plasmin on the activity of MMP-9. Gelatin zymogram evaluation of type IV collagenase in the conditioned medium of THP-1 cells pretreated with the following: (1) none; (2) 5 ng/ml TNF; (3) plasmin (0.04 unit/ml); (4) 5 ng/ml TNF+plasmin (0.04 unit/ml). To prevent the proteolysis of gelatin by plasmin, phenylmethylsulfonyl fluoride (1 mM) was added to the buffered solution after electrophoresis.

Figure 8:
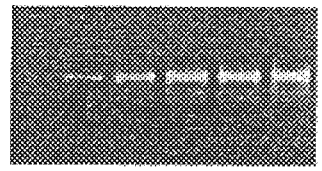

FIG. 8 Gelatin zymogram evaluation of type IV collagenase in the conditioned medium of high density THP-1 cells with or without TNF treatment. Gelatin zymogram of the conditioned medium from THP-1 cells pretreated with the following: (1) none; (2) 0.04 ng/ml TNF; (3) 0.2 ng/ml TNF; (4) 1 ng/ml TNF; (5) 5 ng/ml TNF; (6) 25 ng/ml TNF. The cells were precultured in high density ($1.5 \times 10^6$ cells/ml), washed with RPMI 1640 twice and then used for assay at the same density ($1.5 \times 10^6$ cells/ml).

Figure 9:

FIG. 9 Effect of endotoxin on the serum level of MMP-9. Five female Balb/c mice were treated with galactosamine (18 mg/mouse i.p.) with or without endotoxin (0.3 µg or 1 µg/mouse i.p.). The serum of each mouse was collected immediately before and 10–11 hours after endotoxin treatment. Three µl of the serum was mixed with 30 µl of the sample buffer solution and 15 µl of the mixtures were evaluated by a gelatin zymogram. From left to right, lanes 1 and 2: the serum of mouse No. 1 before and after galactosamine i.p. injection; lanes 3 and 4: the serum of mouse No. 2 before and after galactosamine; lanes 5 and 6: the serum of mouse No. 3 before and after galactosamine and 0.3 µg endotoxin treatment; lanes 7 and 8: the serum of mouse No. 4 before and after galactosamine and 0.3 µg endotoxin treatment; lanes 9 and 10: the serum of mouse No. 5 before and after galactosamine and 1 µg endotoxin treatment. The major band in each lane is MMP-9. This is a typical example of two experiments.

Figure 10:
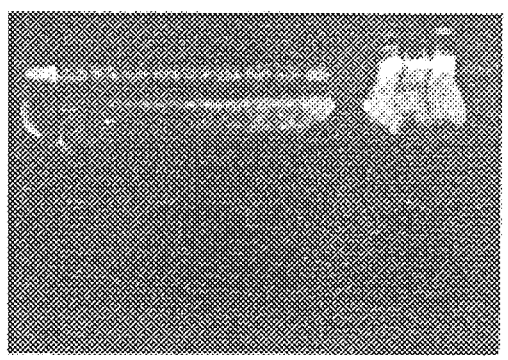

FIG. 10 This figure depicts the zymographic analysis of serum of endotoxin treated mice which are treated with (3aα, 5β, 6α, 7aβ)-4,4'-(hexahydro-2,2-dimethyl-1,3-benzodioxole-5,6-diyl)bis(2,6-piperazinedione) (80) and a control group which was not treated.

Figure 11:
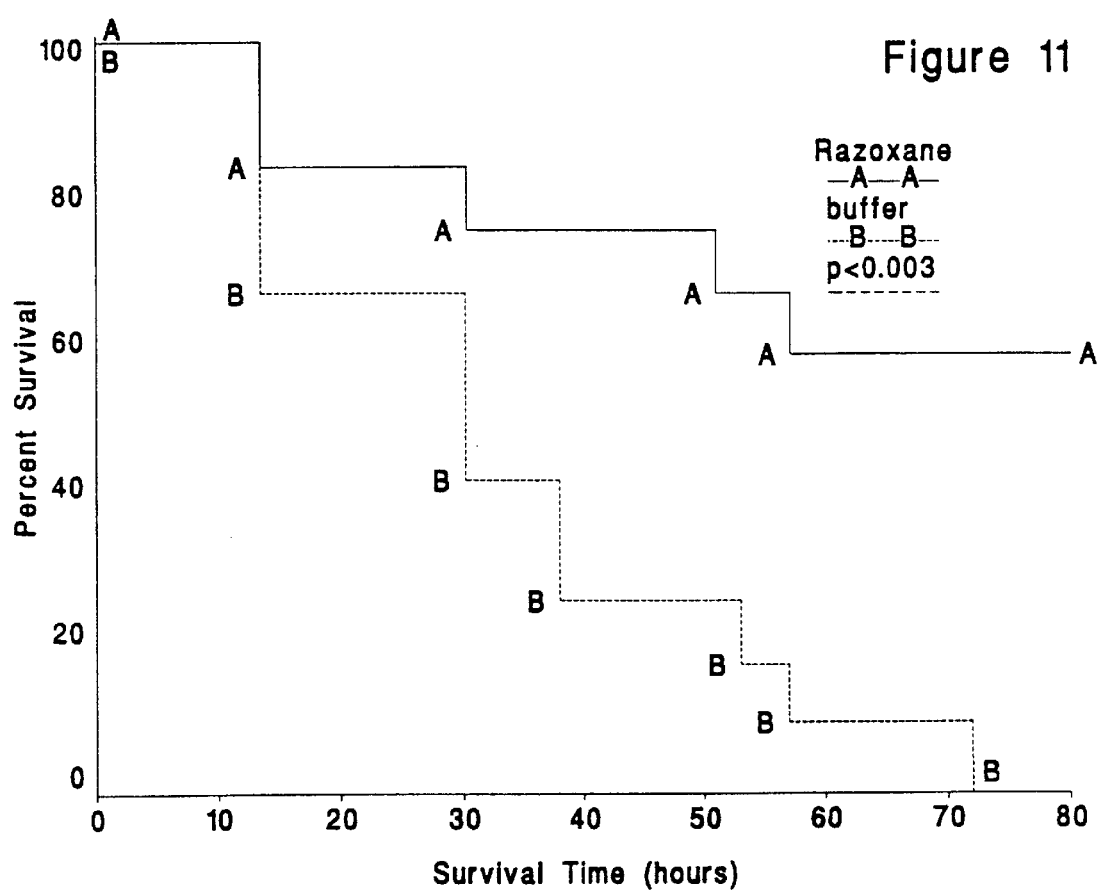

FIG. 11 This figure shows the survival results obtained when twelve Balb/c mice were i.p. administered endotoxin or endotoxin followed by razoxane as described in Example 7.

Figure 12:
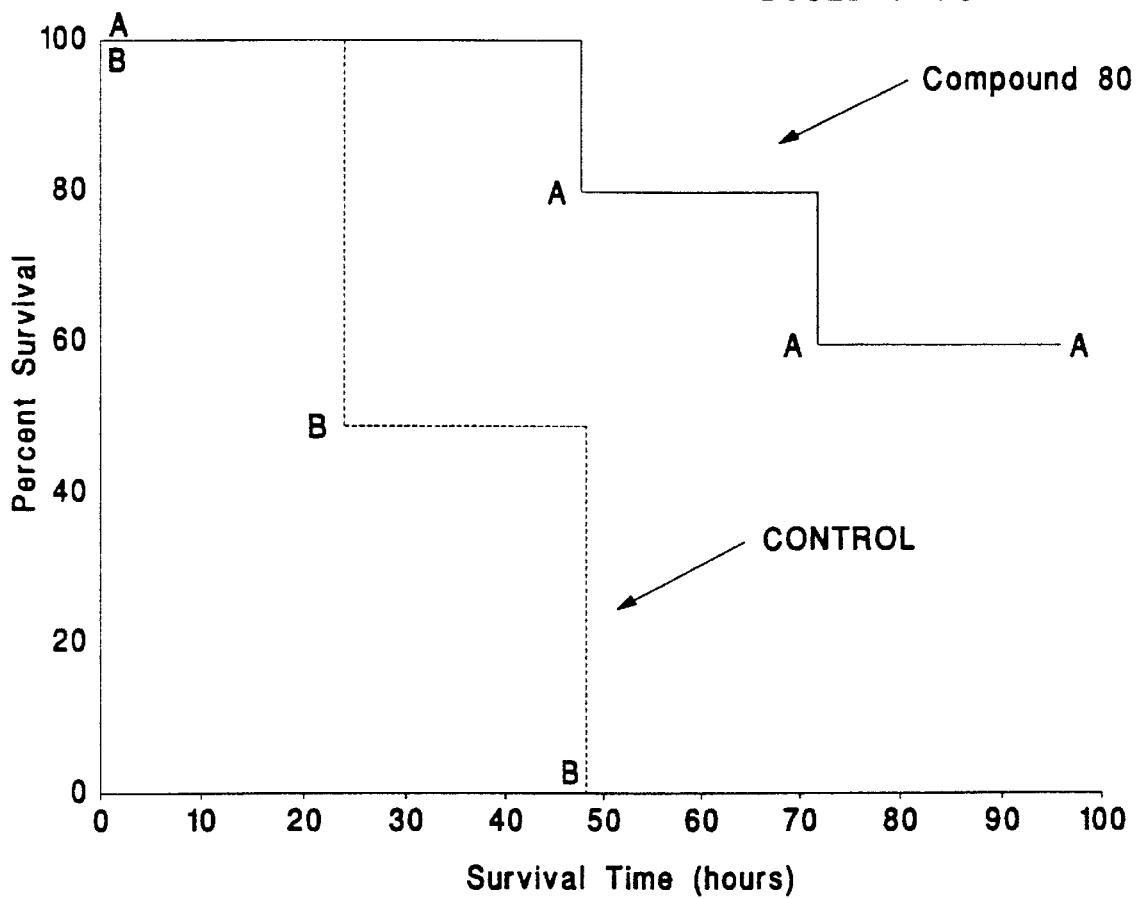

FIG. 12 This figure depicts the effect on survival of endotoxin-treated mice which are treated with (3aα, 5β, 6α, 7aβ)-4,4'-(hexahydro-2,2dimethyl-1,3-benzodioxole-5,6-diyl)bis(2,6-piperazinedione) (80) and a control group which was not treated.

Figure 13:
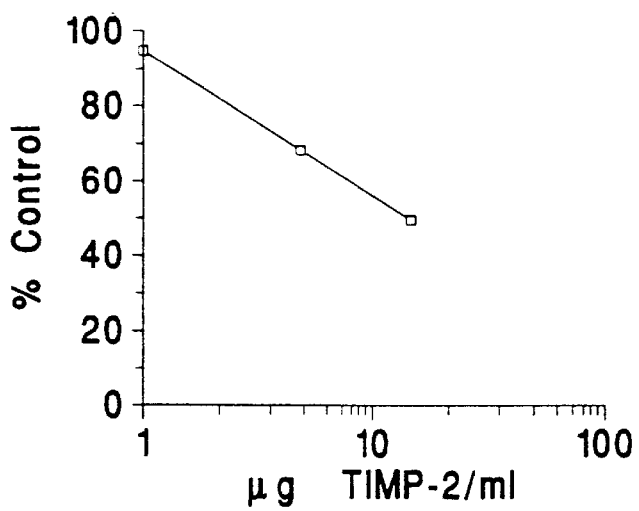

FIG. 13 This figure shows the results of an in vitro invasion assay using HT-1080 cells which are contacted with various concentrations of TIMP-2, the natural inhibitor of the 72 kD inhibitor of type IV collagenase.

Figure 14:
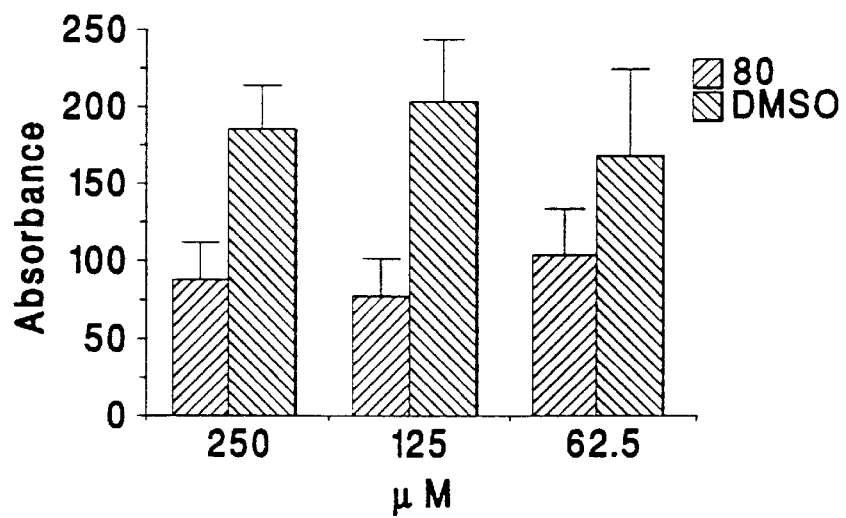

FIG. 14 This figure shows the dose response of (3aα, 5β, 6α, 7aβ)4,4'-hexahydro-2,2-dimethyl-1,3-benzodioxole-5,6-diyl)bis(2,6-piperazinedione) (80) on the invasion of HT-1080 cells.

Figure 15:
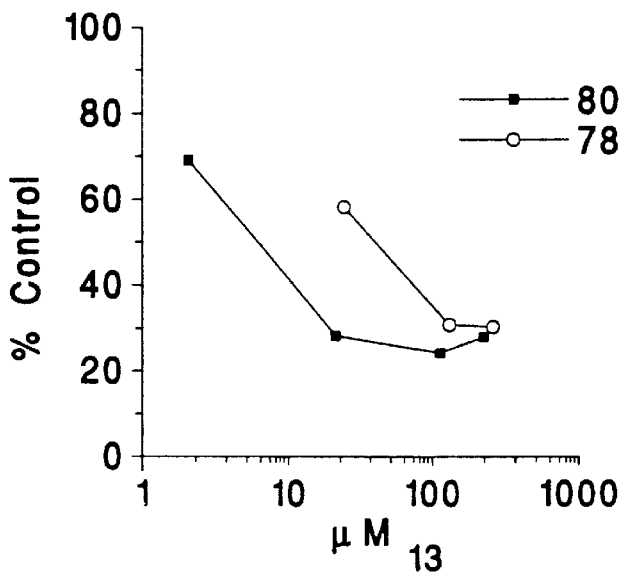

FIG. 15 This figure shows the dose dependent inhibition of collagenase type IV by (3aα, 5α, 6β, 7aα)-4,4'- hexahydro-2,2-dimethyl-1,3benzodioxole-5,6-diyl)bis(2,6-piperazinedione) (78) and (3aα, 5β, 6α, 7aβ)-4,4'-hexahydro-2,2-dimethyl-1,3-benzodioxole-5,6-diyl)bis(2,6-piperazinedione) (80).

Figure 16:
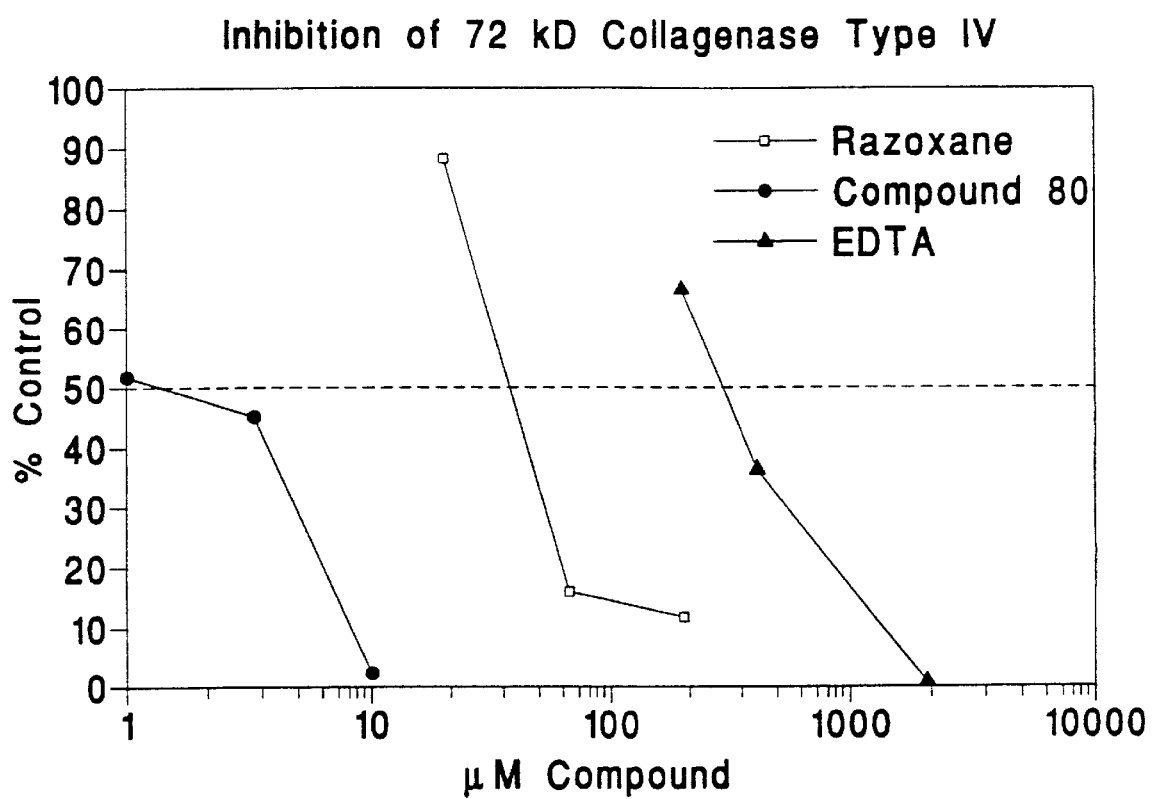

FIG. 16 This figure depicts the results of in vitro inhibition of 72 KD collagenase type IV using razoxane, EDTA and (3aα, 5β, 6α, 7aβ)-4,4'-(hexahydro-2,2-dimethyl-1,3-benzodioxole-5,6-diyl)bis(2,6-piperazinedione) (80).

Figure 17:
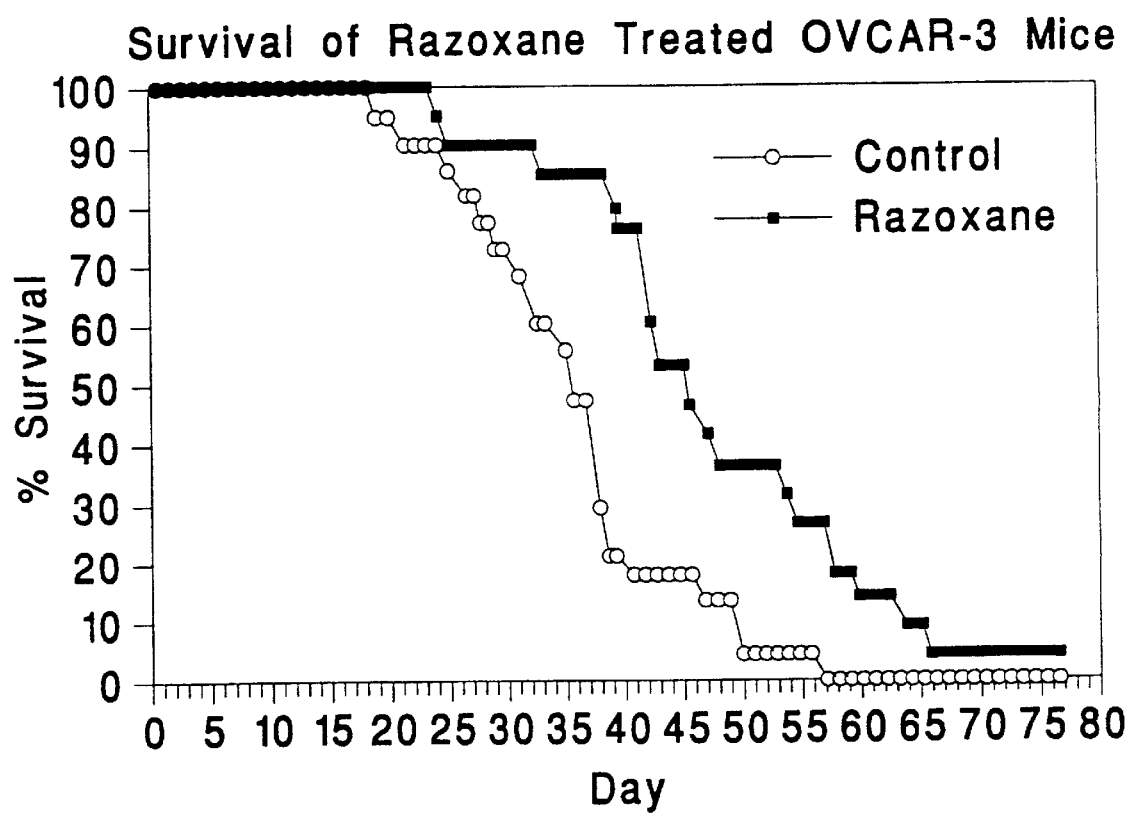

FIG. 17 This figure depicts the effects on survival time of OVCAR-3 treated mice which have been treated with razoxane and a control group which was not treated.

Figure 18:
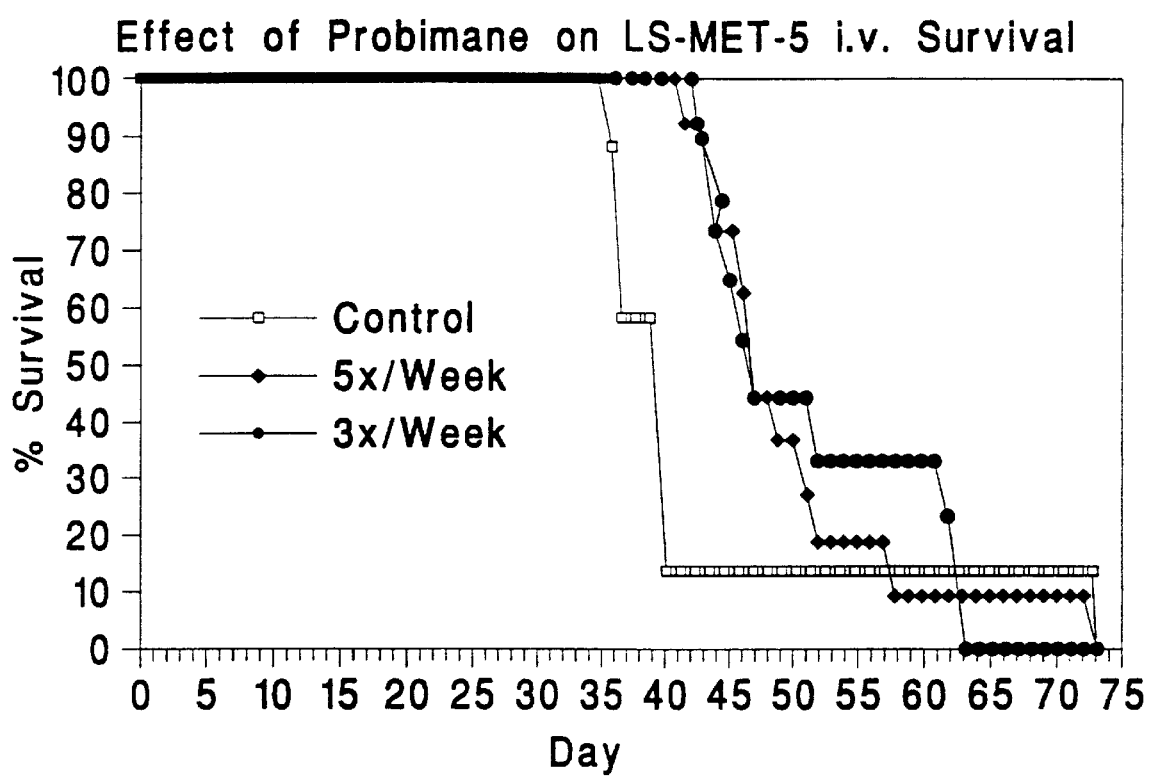

FIG. 18 This figure depicts the effects of probimane on the survival of LS-MET-5 containing mice and an LS-MET-5 control group which were not treated with probimane.

Figure 19:
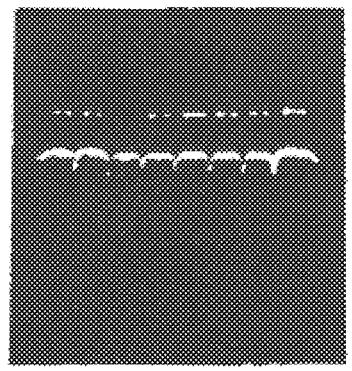

FIG. 19 This figure depicts gelatin zymogram analysis of serum from a monkey which had been intravenously administered OLX-209, an immunotoxin comprising a single chain antibody directed to erbB-2 fused to a cytotoxic fragment of *Pseudomonas exotoxin* via an oligopeptide linker.

Figure 20:
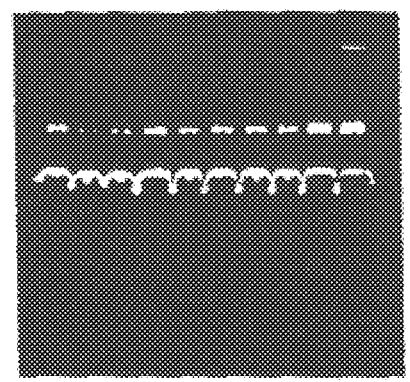

FIG. 20 This figure depicts gelatin zymogram analysis of serum obtained from a monkey which had been intravenously administered OLX-209, an immunotoxin comprising a single chain antibody directed to erbB-2 fused to a cytotoxic fragment of *Pseudomonas exotoxin* via an oligopeptide linker.

DETAILED DESCRIPTION OF THE INVENTION

One object of the present invention is to provide a means for the prevention or treatment of vascular leakage syndrome, in particular SIRS such as septic shock and related disorders by the administration of an effective amount of one or more substances which inhibit the activity of metalloproteinases, e.g., type IV collagenases, such as MMP-9, MMP-2, or by administration of one or more substances which inhibit the expression of metalloproteinases, e.g., collagenase type IV collagenases such as MMP-2 and MMP-9. Suitable metalloproteinase inhibitors will include both competitive and non-competitive type inhibitors. Preferably, the metalloproteinase inhibitor will comprise a type IV collagenase inhibitor, and most preferably an MMP-2 or MMP-9 inhibitor.

A wide variety of metalloproteinase inhibitors are known in the art. Representative of such inhibitors and methods for their production include the inhibitors claimed in the following patents: U.S. Pat. No. 4,367,233, "Inhibitors of Mammalian Collagenase"; U.S. Pat. No. 4,371,465, U.S. Pat. No. 4,371,466, U.S. Pat. No. 4,374,765, "Mammalian Collagenase Inhibitors"; U.S. Pat. No. 4,235,885, U.S. Pat. No. 4,263,293, U.S. Pat. No. 4,297,275, U.S. Pat. No. 4,382,081, U.S. Pat. No. 4,382,081, "Inhibitors of Mammalian Collagenase"; U.S. Pat. No. 4,558,034, "Inhibitors of Bacterial Collagenase"; U.S. Pat. No. 4,276,284, "Prevention of Collagenase induced disease by treatment with collagenase inhibitors"; and U.S. Pat. No. 4,704,383, "Non-AntiBacterial Tetracycline compositions possessing anti-collagenolytic properties and methods of preparing and using same".

Examples of specific substances which inhibit the activity of metalloproteinases, e.g., type IV collagenases, includes, e.g., naturally occurring metalloproteinase inhibitors such as tissue inhibitors of metalloproteinases, e.g., TIMP-1 and TIMP-2, and fragments or derivatives thereof which inhibit metalloproteinase activity. Additionally, metalloproteinase inhibiting substances will include antibodies capable of specifically binding to metalloproteinases, e.g., antibodies which specifically bind to type IV collagenases, e.g., MMP-2 and MMP-9. Suitable antibodies will include, e.g., polyclonal, monoclonal, single chain and chimeric antibodies, which are capable of specifically binding to metalloproteinases such as type IV collagenases and inhibiting the activity thereof.

Examples of metalloproteinase inhibitory substances will further include metalloproteinase receptor proteins or fragments thereof, or antibodies directed to said receptor proteins which may prevent the binding of the particular metalloproteinase which is to be inhibited to its corresponding receptor.

Further, metalloproteinase inhibitors will include other enzymes, e.g., proteases which provide for the inactivation of metalloproteinases, e.g., by the hydrolysis thereof into inactive fragments.

The above described metalloproteinase inhibitory compounds are related in that they for the most part comprise proteins or peptides which are capable of inhibiting metalloproteinases, e.g., type IV collagenases. However, the invention further embraces the use of synthetic metalloproteinase inhibitors, in particular collagenase type IV inhibitors.

Such substances will include, e.g., chelating agents such as EDTA and bis(dioxopiperazine)s. However, the invention is not restricted to the use of chelating agents, but rather embraces the use of any compound(s) which inhibits the activity or expression of metalloproteinases, especially type IV collagenases including, e.g., MMP-2 and MMP-9.

The invention further embraces the use of conjugates or complexes of one or more of the above-mentioned substances which retain the ability to inhibit metalloproteinases and which may further provide for the enhanced stability or targeting thereof to a site, e.g., a site of infection. For example, a synthetic metalloproteinase inhibitor [e.g., a bis(dioxopiperazine) compound] may be conjugated to an antibody, cell receptor, or TIMP protein to direct it to a specific site, e.g., a site of infection or to a collagenase enzyme which is to be inhibited. Such conjugates may afford advantages in that they provide for irreversible inactivation of metalloproteinases, or they may provide for enhanced serum half life of the metalloproteinase inhibitor.

Examples of substances which inhibit the expression of metalloproteinases, in particular, type IV collagenases such as MMP-2 and MMP-9 will include, e.g., substances which regulate the transcription or translation of metalloproteinases, or which regulate the activation of metalloproteinases.

Substances which regulate metalloproteinase transcription will include antisense RNA, e.g., antisense c-Fos RNA and antisense c-Jun RNA. Additionally, compounds which inhibit expression of metalloproteinases will include proteins, such as growth factors which exert a regulatory role in metalloproteinase transcription. For example, transforming growth factor-beta (TGF-β) is a growth factor which exerts an effect on the transcription of matrix metalloproteinases.

As discussed in the Background of the Invention, a particular class of compounds, bis(dioxopiperazine)s, has been established by the in vitro assays described herein to be capable of substantially inhibiting metalloproteinases, including type IV collagenases, in particular MMP-2 and MMP-9 and to be suitable for the treatment of vascular leakage syndrome, and septic shock. These compounds find current usage, e.g., in the treatment of tumor metastasis, psoriasis and for preventing cardiac toxicity caused by doxorubicin.

Therefore, an additional object of the invention is to provide an in vitro method for identifying specific bis(dioxopiperazine)s which are suitable for the treatment of collagenase related disorders, such as vascular leakage syndrome, and septic shock and metastasis by identifying in vitro those bis(dioxopiperazine)s which inhibit the activity of matrix metalloproteinases, e.g., type IV collagenases such as MMP-2 and MMP-9. Moreover, the present invention further provides methods for using said specific bis(dioxopiperazine)s, as anti-metastatic agents and for the treatment of metalloproteinase related disorders such as vascular leakage syndrome and septic shock.

Current methods for screening the therapeutic efficacy of bis(dioxopiperazine)s comprise the administration of such compounds to animals. For example, the anti-metastatic activity of bis(dioxopiperazine) compounds is typically effected by administration to tumor-bearing animals and evaluating the anti-metastatic activity thereof. However, animal testing is disadvantageous because it is both expensive and time consuming.

In contrast, the present invention provides a method for rapidly screening the putative efficacy of candidate bis(dioxopiperazine)s as therapeutic agents, e.g., as anti-metastatic agents or for the treatment of collagenase related disorders and conditions, such as vascular leakage disorder and septic shock by evaluating the ability of such compounds to inhibit type IV collagenases in vitro. Those compounds which substantially inhibit type IV collagenases will then be subjected to in vivo testing to identify those of which exhibit other properties rendering them most suitable for the treatment of metastasis and collagenase related disorders. For example, such compounds should additionally be chemically and biologically stable, serum soluble, and be sufficiently transported to the required site. Thus, the present invention provides an in vitro method for rapidly identifying specific bisdioxopiperazine compounds which are likely candidates for therapeutic usage in the treatment of collagenase related disorders.

This is highly significant since currently available therapeutic bis(dioxopiperazine)s, in particular razoxane, are known to comprise various properties which render such compounds disadvantageous during therapeutic use. As discussed, razoxane exhibits poor water solubility, and also comprises poor chemical and biological stability and is inactively transported to active sites. Moreover, by establishing the putative mechanism for the therapeutic activity of bis(dioxopiperazine)s and the biochemical site of action, the present invention should provide a means for the rational design of bis(dioxopiperazine) structures which exhibit therapeutic activity.

Candidate bis(dioxopiperazine) compounds to be screened for collagenase inhibitory activity will preferably comprise two intact 2,6-dioxopiperazine moieties, although compounds having one or more dioxopiperazine rings may be sufficient for biological activity. Preferably, the linkages between the heterocyclic rings will comprise five or fewer carbons since this seems to result in more effective compounds.

In particular, one or more of the bis(dioxopiperazine) moieties may be substituted by one or more small alkyl, aromatic, heterocyclic, or heterocyclic allyl groups, e.g., methyl, ethyl, propyl, butyl, phenyl, phenylmethyl, substituted phenylmethyl, morpholinomethyl, piperazinomethyl, succinyl- and glutarylmethyl, thiadiazol, piperidinyl, thiazolyl, thiazolylmethyl, and related O, N and S isosters.

Additionally, such candidate compounds may include one or more functional groups which may provide for the enhanced solubility thereof, including, e.g., hydroxyl, polyhydroxy carboxylic acid, hydroxyl derivatives such as acyloxymethyl and amino derivatives exemplified by morpholinomethyl groups, other ionizing functions such as phenols and respective ester products of phenols and carboxyclic acids.

As noted above, preferably the candidate dioxopiperazine compounds will contain at least two intact 2,6-dioxopiperazine moieties, but in addition, the invention embraces tetra(ester) synthetic precursors to the dioxopiperazines, their free carboxylic acids and related derivatives which like EDTA are chelators of potential biological importance. These dioxopiperazine and related chelating functions and their producing derivatives may be attached to a lower aromatic, heterocyclic or lower alkyl group, which aromatic, heterocyclic or lower alkyl groups may in turn be attached to one or more lower alkyl, aromatic or heterocyclic groups. Preferably such alkyl and aromatic groups will comprise from 1 to 6 carbons. The heterocyclic moieties may comprise one or more oxygen, nitrogen or sulfur groups.

The 2,6-bis(dioxopiperazine) rings may be in any orientation, however, compounds wherein the bisdioxopiperazine rings are in a cisoid relationship are expected to exhibit best therapeutic activity. However, compounds wherein the bis(dioxopiperazine) rings are in a trans relationship may also exhibit therapeutic efficacy.

In addition, when cyclohexane analogs are present, and there are hydroxyl or carboxylic acid moieties, preferably such moieties will be substituted cis-anti-cis relative to the dioxopiperazine rings since there is some evidence that this may be important for enhanced water solubility.

Specific examples of bis(dioxopiperazine) compounds which may be evaluated according to the present invention include, e.g., razoxane (4), trans-4,4'-(cyclohexanediyl)bis(2,6)dioxopiperazine (88–93), cis-4,4'-(cyclopropanediyl)bis(2,6)dioxopiperazine (16), tricyclic tetrazaperhydrophenanthrenes (wherein the dioxopiperazine rings maintain a cisoid relationship) (20–21), tricyclic tetrazaperhydroanthracenes (22–23), bimolane, probimane, and isopropylidine derivatives of 4,5-dihydroxy-1,2-cyclohexanediyl-bis(2,6) dioxopiperazine (76–80); (3aα, 5β, 6α, 7aβ)-4,4'-(hexahydro-2,2-dimethyl-1,3-benzodioxole-5,6-diyl)bis(2,6-piperazinedione (80); (3aα, 5β, 6α, 7aβ)-diethyl N,N'-(hexahydro-2,2-dimethyl-1,3-benzodioxole-5,6-diyl)bis[N-(2-ethoxy-2-oxoethyl)] glycine ester (76); (3aα, 5α, 6β, 7aβ)-diethyl N,N'-(hexahydro-2,2-dimethyl-1,3-benzodioxole-5,6-diyl)bis[N-(2-ethoxy-2-oxoethyl)] glycine ester (71); [cis-diethyl N,N'-(4-cyclohexene-1,2-diyl) bis[N-(2-ethoxy-2-oxoethyl)] glycine ester]; (1β, 2β, 4β, 5β)-4,4'-(4,5-dihydroxy-1,2-cyclohexanediyl)bis(2,6-piperazinedione) (88); (1β, 2β, 4α, 5α)-4,4'-(4,5-dihydroxy-1,2-cyclohexanediyl)bis(2,6-piperazinedione) (89); (1α, 2β, 4β, 5β)-4,4'-(4,5-dihydroxy-1,2cyclohexanediyl)bis(2,6-piperazinedione) (90); (1α, 2β, 4β, 5α)-4,4'-(4,5-dihydroxy-1,2-cyclohexanediyl)bis(2,6-piperazinedione) (91); (1α, 2β, 4α, 5β)-4,4'-(4,5-dihydroxy-1,2-cyclohexanediyl)bis(2,6-piperazinedione) (92). Additionally, candidate bis(dioxopiperazine) compounds to be evaluated for efficacy according to the subject in vitro methods may include any of the dioxopiperazine compounds which are disclosed in U.S. Ser. No. 596,364 by Nair et al, Ser. No. 749,514 by Witiak et al, Ser. No. 764,484 by Witiak et al, Ser. No. 251,102 by Witiak et al, Ser. No. 882,258 by Witiak et al and U.S. Pat. No. 4,871,736 to Nair et al and U.S. Pat; No. 4,683,087 to Witiak et al which are incorporated by reference herein.

This list is meant to be exemplary, and by no means exhaustive, since the present in vitro screening method should be applicable to any available bis(dioxopiperazine) compound.

The ability of candidate compounds to inhibit matrix metalloproteinases, in particular type IV collagenases such as MMP-2 and MMP-9 may be tested using standard matrix metalloproteinase assays. Typically such assays measure the ability of matrix metalloproteinases to catalyze the breakdown of gelatin or collagen. Appropriate assay conditions may be found, e.g., in U.S. Pat. No. 4,743,587; Cawston et al., *Anal. Biochem.* (1979) 94: 340–345 and Weingarten et al., *Biochem. Biophys. Res. Commun.* (1984)134: 1184–1187.

However, any standard assay for measuring metalloproteinase activity may be used. Such assays will comprise determining whether and to what extent a candidate compound inhibits the activity of a particular matrix metalloproteinase in vitro.

In a preferred embodiment, the therapeutic activity of candidate bis(dioxopiperazine)s will be biochemically assayed on the basis of the relative ability of the compound to inhibit a collagenase, preferably a type IV collagenase, and most preferably the 72 or 92 kilodalton form of type IV collagenase, i.e., MMP-2 or MMP-9 respectively. These matrix metalloproteinases are thought to play an essential role in the degradation of basement membranes. Such degradation is believed to be related to the ability of cells (e.g., tumors) to invade basement membranes which is believed to be involved in metastasis or vascular leakage syndrome and septic shock.

Such biochemical assays may include one or more of the following methods:

i) measuring in vitro the ability of a candidate compound to inhibit biochemical degradation of gelation by a collagenase, e.g., MMP-2 or MMP-9;

ii) measuring in vitro the ability of a candidate compound to inhibit biochemical degradation of collagen IV by type IV collagenases, e.g., MMP-2 or MMP-9; and iii) measuring in vitro the ability of a candidate compound to inhibit gelatinase activity of cell supernatants (containing additional metalloproteinases) run on SDS-PAGE containing gelation, known as a zymogram.

In general, compounds which exhibit collagenase inhibitory activity in the above assays should possess potential utility for the treatment of septic shock, vascular leakage syndrome and other collagenase related disorders.

Additionally, the metalloproteinase inhibitory activity of candidate bisdioxopiperazines may also be determined on the basis of in vitro cellular attachment assays and on the basis of mobility and invasion through basement membranes. Such in vitro assays may include one or more of the following methods:

i) determining whether the candidate compound inhibits attachment to basement membrane proteins;

ii) determining in a modified Boyden chamber assay whether the candidate compound inhibits directed motility of cells (e.g., tumor cells) to a chemoattractant; and iii) determining in the assay of (ii) whether the particular compound inhibits in vitro invasion in the presence of isolated basement membrane proteins.

Finally, the ability of a candidate bis(dioxopiperazine) compound to inhibit metalloproteinases, e.g., collagenase type IV, may be determined by measuring in vitro its effect on the expression of endogenous metalloproteinase level of inhibitors, such as TIMP's, in tissue culture, or by measuring its effect on transcription of type IV collagenases or on the activation of type IV collagenases.

Specifically, collagenase or inhibitor expression and transcription will be compared in tissue cultures which contain the candidate bis(dioxopiperazine) to control tissue cultures which lack any bis(dioxopiperazine) compound. Inhibitor expression and transcription may be determined, e.g., by Northern blot analysis using one or more cDNA probes capable of specifically binding to the particular inhibitor or metalloproteinase MRNA. Alternatively, inhibitor expression may be determined by Western blot analysis using antibodies capable of specifically binding to the particular inhibitor which expression is to be measured.

As discussed supra, the invention comprises a method of treatment of vascular leakage syndrome and septic shock by administering an effective amount of one or more metalloproteinase inhibitors, preferably one or more collagenase inhibitors, and still more preferably one or more type IV collagenase inhibitors, or one or more compounds which inhibit the expression of activation thereof. In addition, the invention provides a method of treating any collagenase related disorder by administering one or more bisdioxopiperazine compounds which have been established in vitro to inhibit collagenase(s), especially type IV collagenases.

These inhibitors may also be complexed or conjugated to targeting moieties, e.g., antibodies or receptor proteins. In addition, these compounds may be administered in conjunction with other septic shock therapeutics, or other therapeutics currently used for the treatment of collagenase related disorders. Representative of such septic shock therapeutics includes, e.g., plasma volume expanders, e.g., dextran, albumin, etc.

Treatment of septic shock according to the subject invention should alleviate some or all of the deleterious effects of septic shock, i.e., tachycardia, hypotension, peripheral cyanosis, oliguria, edema, and end-organ failures, e.g., kidney, lung or liver failure. A particular advantage of the present invention is that treatment may be effected at any stage of sepsis or septic shock, in particular, the latter stages of this disease condition which are generally non-responsive to conventional septic shock treatments.

The effective amount of metalloproteinase inhibitor which is administered will vary dependent upon factors including the particular inhibitor compound(s) administered, the severity of the disease condition, and the particular disease condition which is being treated. Typically an effective amount of the inhibitor which is administered to the patent will range from at least 0.1 mg/kg of body weight per day to about 20 mg/kg of body weight per day. Preferably, the amount of inhibitor will range from about 0.1 mg/kg of body weight per day to about 5 mg/kg of body weight per day.

The metalloproteinase inhibitor, preferably a bis (dioxopiperazine) compound or a natural inhibitor such as TIMP-1 or TIMP-2, may be administered in solution, preferably an aqueous solution having a concentration of inhibitor which will typically range from about 0.5 mg/ml to about 10 mg/ml. Preferably, the concentration of the inhibitor in the aqueous solution will range from about 1 mg/ml to about 2 mg/ml.

The metalloproteinase inhibitor may be administered prophylactically, chronically or acutely. For example, such compounds may be administered prophylactically to patients exhibiting infections in order to prevent the onset of vascular leakage syndrome or septic shock.

Chronic administration of metalloproteinase inhibitors, e.g., bis(dioxopiperazine)s, will typically be effected for chronic collagenase related disease conditions including, e.g., inflammatory disorders such as arthritis.

Acute administration of metalloproteinase inhibitors, e.g., bis(dioxopiperazine) compounds, will be effected, e.g., to treat the advanced stages of vascular leakage syndrome and septic shock.

The metalloproteinase inhibitor may be administered by any pharmaceutically acceptable means, e.g., oral, intravenous or subcutaneous. Preferably, the inhibitor will be administered by intravenous infusion.

The metalloproteinase inhibitor may also be administered through a slow-release or time-release method. This may, e.g., be advantageous if a chronic collagenase related disorder is being treated, as a means of avoiding repeated administration. Such methods include, e.g., the administration of polymeric pharmaceutical formulations, osmotic pumps, or time release patches which allow for the release over time of an effective amount of the inhibitor(s).

Preferably, the metalloproteinase inhibitor(s) will be comprised in an aqueous solution which includes a pharmaceutically acceptable carrier such as physiological saline, non-toxic buffers or fillers, 5% dextrose, and plasma volume expanders.

This composition may further contain other septic shock therapeutics (if septic shock is to be treated), or other compounds suitable for treatment of collagenase related disease conditions (if a collagenase related disorder is to be treated).

As discussed supra, another object of the invention is the treatment of toxicity or disease conditions caused by endogenous cytokine production (e.g., interleukins, interferons, tumor necrosis factors, such as IL-1, IL-2 and TNF) or by the administration of cytokines; wherein such treatment will comprise the administration of an effective amount of one or more metalloproteinase inhibitors, in particular collagenase inhibitors, and preferably type IV collagenase inhibitors.

It is believed that cytokines, e.g., TNF and IL-1, are involved in the occurrence of severe hypotension during septic shock. Additionally, applicants believe that metalloproteinases, in particular collagenases, are also involved in the mediation of septic shock by cytokines, e.g., TNF and IL-1. Accordingly, the present invention further provides a method for the treatment of cytokine mediated diseases and toxicity which are further mediated by collagenase.

Moreover, vascular leakage syndrome is also a side effect of cytokine therapy, in particular, IL-2 therapy (Puri et al, *Cancer Research,* (1989), 49, 969). Accordingly, the administration of metalloproteinase inhibitors, preferably collagenase inhibitors, and most preferably type IV collagenase inhibitors should prevent or alleviate the onset of vascular leakage syndrome as a side effect of cytokine therapy, e.g., IL-2 therapy, and for the treatment of cytokine mediated diseases. The administration of such collagenase inhibitors may be effected as described supra when using such inhibitors for the treatment of vascular leakage syndrome and septic shock.

As discussed supra, metalloproteinase inhibitors and substances which inhibit metalloproteinase expression, and more specifically type IV collagenase inhibitors and substances which inhibit type IV collagenase expression, e.g., MMP-2 and MMP-9 are suitable for the treatment of any septic shock or vascular leakage related condition as well as conditions which typically precede the onset of vascular leakage syndrome, e.g., sepsis syndrome and sepsis. Most typically, such conditions result from bacterial infection. However, there are other mediators of vascular leakage syndrome and septic shock, including e.g., cytokines and immunotoxins which are also treatable by the administration of metalloproteinase inhibitors.

For example, Vittetta et al, *Cancer Research,* Vol. 51, pp. 4052–4058 (1991), report that the administration of a ricin based immunotoxin during phase I clinical trials resulted in drug-related toxic side effects including vascular leakage syndrome, fever, anorexia and myalgia. However, prior to the present invention, it was not known that immunotoxin administration may result in enhanced serum metalloproteinase levels, in particular enhanced type IV collagenase levels, and specifically MMP-9, and that these enzymes are the mediator of immunotoxin induced vascular leakage syndrome. Infra, the present inventors provide convincing in vitro evidence that the administration of an immunotoxin, specifically a *Pseudomonas exotoxin* derivative containing immunotoxin, gives rise to enhanced serum levels of the type IV collagenase MMP-9. This was demonstrated in blood serum obtained from monkeys which had been previously intravenously administered a *Pseudomonas exotoxin*.

Therefore, the invention also provides a method of treating or preventing vascular leakage syndrome or septic shock induced by the administration of immunotoxins comprising administering prior, concurrent or after immunotoxin therapy an amount of at least one metalloproteinase inhibitor, preferably a collagenase inhibitor, which is sufficient to prevent or alleviate the toxic side effects or immunotoxin administration.

The effective amount and dosage regimen will largely depend upon the relative toxicity of the immunotoxin and its toxic side effects, in particular vascular leakage syndrome and septic shock. The metalloproteinase inhibitor, and preferably a collagenase inhibitor, will ideally be administered prior to the onset of immunotoxin administration, so as to prevent the onset of vascular leakage syndrome or septic shock. However, administration may be effected concurrent or proximate to immunotoxin administration, e.g., ranging from about 24 hours before to about 24 hours after immunotoxin administration.

The typical dosage of the metalloproteinase inhibitor will again vary dependent upon factors such as the condition of the particular subject being treated, the particular metalloproteinase inhibitor, whether the particular inhibitor is used in conjunction with other metalloproteinase inhibitors or singularly. For example, an effective amount of inhibitor will typically range from at least about 0.1 mg/kg of body weight per day to about 20 mg/kg of body weight per day. Preferably, the amount of inhibitor will range from about 0.1 mg/kg of body weight per day to about 5 mg/kg of body weight per day, with administration being effected by the methods and in formulations such as described supra.

Metalloproteinase inhibitor administration, and specifically collagenase inhibitor administration, may be used to treat or prevent vascular leakage syndrome or septic shock induced by any immunotoxin. In the subject application, immunotoxin refers to any toxin or active fragment fused or conjugated to a targeting moiety, e.g., antibody or fragment, or receptor protein.

Examples of toxins include by way of example cytotoxic drugs, enzymatically active toxins of bacterial or plant origin, toxic fragments thereof (e.g., "A chain" of a ricin toxin). Enzymatically active toxins and fragments thereof include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), momordica charantia inhibitor, curcin, crotin, sapaonaria officinalis inhibitor, gelonin, mitogellin, restrictocin, phenomycin, and enomycin, as well as cytotoxic fragments thereof made by enzymatic or recombinant methods. Cytotoxic drugs include anti-cancer drugs such as methotrexate, daunorubicin, doxorubicin, radionuclides, superoxide dismutase and other therapeutic enzymes, etc. This list is meant to be representative and by no means exhaustive.

Suitable targeting moieties for use in immunotoxins include, by way of example, antibodies and binding fragments thereof, e.g., Fab fragments, (Fab)$_2$, (Fab$^1$)$_2$, recombinant antibodies, and single chain antibodies. Most typically, the targeting moiety will specifically bind to an antigen expressed on cancer cells. In the examples, the targeting moiety contained in the immunotoxin comprises a single chain antibody which specifically binds to erbB-2, a receptor known to be expressed on many cancer cell types.

The invention further provides in vitro assay methods for identifying those patients who are believed to be at substantial risk for developing vascular leakage syndrome and SIRS such as septic shock. In particular, this method will comprise obtaining a serum sample from a patient exhibiting some of the early warning signs of vascular leakage syndrome and/or septic shock (e.g., patients who comprise bacteremia) and measuring the serum concentration of matrix metalloproteinases, in particular collagenases, and most preferably type IV collagenases such as MMP-2 and MMP-9, comprised therein. The serum concentration of matrix metalloproteinase, e.g., MMP-2 and MMP-9 will be compared to normal levels of matrix metalloproteinase expression, in particular MMP-2 and MMP-9.

Such assays may be effected using standard assay techniques, e.g., ELISA, immunofluorescence assays, or radioimmunoassays, using immunological probes capable of specifically binding to a matrix metalloproteinase, e.g., MMP-2 or MMP-9. Preferably, monoclonal antibodies to MMP-2 or MMP-9 will be utilized. Alternatively, enhanced expression may be determined based on metalloproteinase activity, in particular type IV collagenase activity.

Patients who demonstrate higher than normal serum levels of matrix metalloproteinase expression or activity, e.g., on the order of at least 1.5 times the level of normal matrix metalloproteinase activity, will then be prophylactically treated with one or more matrix metalloproteinase inhibitors, preferably one or more type IV collagenase inhibitors, and most preferably one or more MMP-2 or MMP-9 inhibitors.

The examples set forth below are included for illustrative purposes and are not intended to in any way limit the scope of the invention.

EXAMPLE 1

This example studies the effects of TNF and IL-1 on the release of MMP-9 from human monocytes.

Cell culture: THP-1 cells were cultured in RPMI 1640 supplemented with 10% heat inactivated FCS and 3–5×10$^-$$^5$M 2-ME. All cells were incubated in a humidified atmosphere of 10% CO$_2$, in air at 37° C. The cells in the growing phase (3–5×10$^5$ cells/ml) were harvested, washed twice with RPMI-1640 and then incubated in serum-free RPMI 1640 in the presence or absence of either IL-1, IL-4, IL-6, IFN-gamma or TNF for 16–24 h. The serum-free conditioned medium was collected and spun at 500×g for 5 min. to remove the cells. The supernatant (1 ml) was concentrated by ultrafiltration (Amicon YM 30 membrane; Amicon, Beveley, Mass.) to remove low molecular weight molecules. The final volume was adjusted with double distilled water to 150 μl and the solution was stored at −20° C.

Preparation of human primary monocytes: Human PBMC were isolated from the leukapheresed blood of normal individuals after Ficoll-Hypaque gradient centrifugation (Boyum, *Scand. J. Clin. Lab. Invest.*, (1968) 21 (Supp. 97), 77). The interface cells were washed twice in pyrogen-free PBS, then resuspended in PBS containing 50 μg/ml of gentamicin sulfate and 1% human serum albumin (elutriation buffer) in preparation for separation by countercurrent centrifugal elutriation. A Beckman system (Stevenson & Fauci, *Manual of Macrophage Methodology*, (1981), Herscowitz et al., editors, N.Y. p. 75) consisting of a J6M centrifuge and a JE-6 elutriatior rotor (Beckman Instruments, Fullerton, Calif.) was used for this procedure. PBMC that had been suspended in buffer were pumped directly into the elutriation chamber of the countercurrent centrifugal elutriation system and lymphocytes were subsequently eluted with elutriation buffer using increasing flow rates while maintaining a constant rotor speed of 2,000 rpm. The monocytes were washed twice, then resuspended in unsupplemented RPMI 1640. Viability as determined by trypan blue exclusion was 99%, and 90 to 95% were positive for the monocytelmacrophage marker Leu M3 (Becton Dickinson, Mountain View, Calif.) and MO2 (Coulter Immunology, Hialeah, Fla.).

Assays for type IV collagenolytic and gelatinase activities: The gelatinase activity of the cell conditioned medium was detected by using gelatin zymogram (10% acrylamide gel containing 0.1% gelatin; Novex, San Diego, Calif.) as described previously (Herron et al. 1986, Heussen et al. 1980). After electrophoresis, the gel was treated with 2.5% triton X-100 to remove sodium dodecyl sulfate and then incubated in a buffered solution (20 mM Tris, 150 mM NaCl, 5 mM CaCl$_2$, 0.05% Brij, pH 7.5) at 37° C. for 18 h so that gelatinase can degrade the gelatin. For the conditioned medium of the cells pretreated with plasmin, phenylmethylsulfonyl fluoride (1 mM) was added to the buffered solution to inhibit the proteolysis of the gelatin by plasmin. The degradation of gelatin by gelatinase was detected by staining the gel with 0.5% Coomassie brilliant blue R-250 (Bethesda Research Laboratory, Bethesda, Md.). The type IV collagenolytic activity was determined by first activating the proenzyme with 1.0 mM APMA at 37° C. for 1 h. Following incubation with APMA, the type IV collagenase activity was assayed by using $^3$H-labeled type IV collagen as a substrate according to the method described by Liotta et al, *Biochem.*, (1981) 20, 100.

Effects of TNF and other cytokines on the release of type IV collagenase from a human monocytic cell line: To evaluate the effect of TNF on the release of type IV collagenase(s) from monocytes, THP-1, a human monocytic cell line, was used as a model. After 18 h incubation of THP-1 cells in RPMI 1640 supplemented with rTNF, gelatin zymogram analysis showed that the level of MMP-9 in the cell conditioned medium was increased by rTNF (0.04–25 ng/ml) in a concentration-dependent manner (FIG. 1A & B). In contrast, the amount of MMP-2 showed little, if any, increase. Interestingly, TNF at high concentrations (≧500 ng/ml) slightly increased the amount of MMP-2 and a higher molecular weight molecule (≧200,000 KD) which exhibited gelatinase activity (FIG. 2, lane 5). The potentiating effect of rTNF was observed only after the cells were incubated with rTNF (FIGS. 1 & 2); mixing rTNF directly with the cell conditioned medium showed little increase in the gelatinase activity of MMP-9. TNF at the concentrations used did not cause any change in the viability of THP-1 cells during the 18–24 h incubation time. These results suggest that although TNF does not directly affect the gelatinase activity of MMP-9, it enhances the release of MMP-9 from the THP-1 cells.

To evaluate if other cytokines besides TNF have potentiating effect(s) on the release of MMP-9, cytokines that have immunomodulating effects on monocytes/ macrophages such as IL-1, IL-4, IL-6 and IFN-gamma were examined. Pretreatment of the cells with rIL-4 (up to 25 ng/ml) or rIFN-gamma (up to 20 ng/ml) caused little if any increase in the amount of the MMP-9 in the conditioned medium as indicated by the gelatin zymogram (FIG. 2 lanes 2 & 4). However, the amount of MMP-9 in the THP-1 cell conditioned medium was elevated by rIL-6 and rIL-1 (FIG. 2 lanes 3 & 6), indicating that IL-1 and IL-6, like TNF, may affect the release of MMP-9.

Distinguishing the effects of TNF from that of IL-1 and IL-6 on the release of type IV collagenase from human monocytic cell line: To evaluate whether the potentiating effects of IL-1 and IL-6 are mediated via TNF or vice versa, THP-1 cells were incubated with either rTNF, rIL-1 or rIL-6 in the presence of anti-TNF, anti-IL-1 or anti-IL-6 antibodies. As shown in FIG. 3, the ability of TNF to increase the level of MMP-9 in the cell conditioned medium (lane 2) was decreased by anti-TNF (lane 3) but not anti-IL-1 antibodies (lane 4). Similarly, the enhancing effect of IL-1 (lane 5) was decreased by anti-IL-1 (lane 7) but not anti-TNF antibodies (lane 6). Anti-TNF or anti-IL-1 antibodies alone had no effect on the release of MMP-9 from THP-1 cells (lanes 8 & 9). Interestingly, although the potentiating effect of IL-6 on the release of MMP-9 (FIG. 4 lane 2) was diminished by anti-IL-6 (FIG. 4 lane 3) but not anti-IL-1 antibodies (data not shown), it was also decreased by anti-TNF antibodies (FIG. 4 lane 8). Anti-IL-6 antibodies did not interfere with the enhancing effects of TNF (FIG. 4 lanes 4 & 5) or IL-1 (lanes 6 & 7). These results indicate that the increased release of MMP-9 from THP-1 cells by TNF is not via IL-1 or vice versa while that caused by IL-6 is at least in part mediated via extracellular TNF.

Effects of TNF on the release of type IV collagenase from human primary monocytes: To verify that the effect of TNF is not limited to the THP-1 cell line, human primary monocytes were also used. Gelatin zymogram analysis of the cell conditioned medium showed that rTNF increased the release of MMP-9 from the purified human primary monocytes in a concentration-dependent manner (FIG. 5 lanes 2–4). This effect of rTNF was specifically inhibited by the addition of anti-TNF antibodies (FIG. 5 lanes 5–7). The activity of MMP-9 in the cell conditioned medium of the primary monocytes was further evaluated by type IV collagenolytic assay. It was found that the conditioned medium of the rTNF treated human primary monocytes contained more type IV collagenase than that of the untreated cells and the effect of rTNF correlated well with the period of incubation (FIG. 6). These results thus indicate that TNF increases the release of MMP-9 from human monocytes.

Influence of proteolvtic enzymes and cell density on the activity of MMP-9: Since the 92 KD protein band is a latent form of MMP-9, we wanted to determine if TNF can potentiate the release of 84 KD active form of MMP-9 in the presence of proteolytic enzymes such as plasmin. The THP-1 cells were therefore treated with plasmin in the presence or absence of rTNF. As shown in FIG. 7, the conditioned medium from cells pretreated with rTNF had the 92 KD band (lane 2) while that from cells pretreated with plasmin (0.04 units/ml) had little gelatinolytic activity (lane 3). Combined treatment of the cells with plasmin and rTNF (5 ng/ml) caused the release of not only 92 KD but also an 84 KD gelatinase into conditioned medium (lane 4). In the absence of THP-1 cells, plasmin alone or the mixture of plasmin and TNF showed little gelatinolytic activity (data not shown). These results indicate that TNF and plasmin may cause the release and activation of MMP-9 from monocytic cells.

To examine whether the cells can activate the latent form of MMP-9 without the addition of proteolytic enzymes such as plasmin, the THP-1 cells were cultured in higher density ($1.5 \times 10^6$ cells/ml), washed and treated with increasing concentrations of rTNF (0.04–25 ng/ml). FIG. 8 shows that under this condition, TNF treatment not only increases the release of 92 KD but also the formation of 84 KD gelatinolytic protein in the conditioned medium to a detectable level, indicating that when the cells accumulate locally they may carry sufficient proteolytic enzymes to activate the latent form of MMP-9.

In summary, TNF and IL-1 stimulate the release of MMP-9 from human monocytes. Since TNF and IL-1 are principal mediators of the inflammatory tissue destruction (Timpl et al., *Meth. Enzymol.* (1987), 145, 363 (1987) and Vracko, *Am. J. Pathol.* (1974), 77, 314), the inhibition of TNF and IL-1 effects is useful for the treatment of inflammation and septic shock. If MMP-9 turns out to be the mediator for the tissue destructive effects of those two cytokines, then even inhibition of both TNF and IL-1 might not be effective in time for the treatment of septic shock once MMP-9 has been released. In this case, the inhibitors of MMP-9 such as TIMP-1, TIMP-2 or other such metalloproteinase inhibitors would be more useful.

EXAMPLE 2

This example shows the production of endogenous type IV collagenase inhibitor such as TIMP-2.

TIMP-2 Production

Recombinant TIMP-2 protein was produced by infection of a monkey kidney cell line (Vero) with a recombinant vaccinia virus, vac-pSC59TIMP-2, containing a human TIMP-2 cDNA driven by a vaccinia promoter. Subconfluent monlayers of Vero cells grown in EMEM medium containing 5% fetal bovine serum were infected with vac-pSC59TIMP-2 virus at a multiplicity of infection of five plaque forming virus particles per cell in the same medium. After 1–2 h for incubation for viral attachment, the medium was changed to a serum-free medium (optiMEM, Life Technologies) for protein production. After 36–48 hours the medium is collected and cells removed by centrifugation. The TIMP-2 containing medium is passed immediately over a column containing immobilized anti-TIMP-2 monoclonal antibody. After washing away the non-specific protein, the affinity column is eluted with buffer at pH 2.5. The $A_{280}$ containing material is dialyzed against sodium acetate buffer, pH 6.0, and loaded on a CM-sepharose column. The bound protein, free of any contaminating nucleic acid, is eluted in 200–400 mM NaCl. The TIMP-2 protein at this stage is approximately 95% pure as measured by SDS-PAGE or by reverse phase HPLC. This protein has the same specific activity as native TIMP-2 as measured by inhibition of gelatinase activity of the human 72 kD type IV collagenase. To inactivate any contaminating vaccinia virus, the protein solution is treated with detergent, NP40, before the CM-sepharose purification step.

EXAMPLE 3

This example shows the effects of type IV collagenase inhibitors on septic shock induced by galactosanine and septic shock mediators.

Septic shock induced by galactosamine and TNF without TIMP-2 treatment:

Two-BALB/C mice were injected with 18 mg of D-galactosamine and 5 μg of recombinant human TNF. Both mice were noticeably sick within 7 hrs and died within 9.5 h.

Septic shock induced by galactosamine and TNF with TIMP-2 treatment:

One BALB/C mouse was injected with 18 mg of D-galactosamine and 5 μg of recombinant human TNF. After 30 minutes 50 μg of TIMP-2 was injected i.p. and another 50 μg of TIMP-2 was injected i.v., additional 50 μg of TIMP-2 was injected i.p. 5 h. later. The mouse did not show any sickness after 7 h. and was still alive after 7 days.

Septic shock induced by galactosamine and endotoxin without TIMP-2 treatment:

Seven BALB/C mice were injected with 18 mg of D-galactosamine and 1 μg of endotoxin. (Unless specified otherwise, the endotoxin used was lipopolysaccharide from E. coli 026:B6). All except one mouse showed sickness by 6.5 h. All except one died within 13.5 h. (2 died after 9.5 h., 2 died after 12.5 h.). One survived for 24 h. and then died shortly after the 24 h. period.

Septic shock induced by galactosamine and endotoxin with TIMP-2 i.p. and i.v. treatment.

Five BALB/C mice were injected with 18 mg of D-galactosamine and 1 μg of endotoxin. After 2.8 h., 40 μg of TIMP-2 was injected i.p. Two mice also received 10 μg of TIMP-2 i.v. while the other three mice received 10 μg TIMP-2 injection in the tail. Three mice showed sickness after 6.3 h. An additional 50 μg of TIMP-2 was injected i.p. to all 5 mice after 6.5 h. Two mice died after 13.3 h. and another died after 15 h. The two mice that got i.v. injection of TIMP-2 were sick but survived for more than 48 h. One of these two mice died at 54 h., while the other recovered and was syndrome free after 72 h.

Septic shock induced by galactosamine and endotoxin without TIMP-2 treatment:

Five BALB/C mice were injected with 18 mg of D-galactosamine and 1 μg of endotoxin. All except one mouse died within 24 h.; the surviving mouse was very sick and died after 48 h.

Septic shock induced by galactosamine and endotoxin with TIMP-2 subcutaneous treatment:

Five BALB/C mice were injected with 18 mg of D-galactosamine and 1 μg of endotoxin. Every 20–30 minutes 10–20 μg of TIMP-2 were injected subcutaneously, for a total dose of 150–200 μg/mouse. Two of the five survived, recovered in 24 h. and resumed normal behavior.

Septic shock induced by galactosamine and endotoxin without razoxane treatment:

Ten BALB/C mine were injected i.p. with 18 mg of D-galactosamine and 1 μg of endotoxin. Three units of heparin were given i.v. and 10 units heparin were given subcutaneously at 30 min to prevent intravascular coagulation. All died within 24 h.

Septic shock induced by galactosamine and endotoxin with razoxane treatment:

Ten BALB/C mice were treated with razoxane (100 μg/g body weight i.p., dissolved in 1% carboxymethyl-cellulose in normal saline). The mice were then injected i.p. with 18 mg of D-galactosamine and 1 μg of endotoxin. Three units of heparin were given i.v. and 10 units heparin were given subcutaneously to each mice at 30 min. Two out of ten mice survived more than 24 h and recovered later on.

EXAMPLE 4

This example shows the effect of type IV collagenase inhibitor, razoxane, on septic shock induced by i.v. injection of endotoxin from E. coli 026:B6.

Septic shock induced by endotoxin without razoxane treatment:

Two retired bred BALB/C mice were injected with 100 μg of endotoxin and 3 units of heparin i.v., followed by 10 units heparin subcutaneously. Another two mice were treated the same except with 200 μg of endotoxin. All died within 24 h.

Septic shock induced by endotoxin with razoxane treatment:

Six retired bred BALB/C mice were treated with razoxane (100 μg/g body weight i.p.). The mice were then injected with 200 μg of endotoxin and 3 units of heparin i.v., followed by 10 units heparin subcutaneously. Two out of six mice survived more than 24 h. and recovered later on.

EXAMPLE 5

This example shows the effect of endotoxin on serum level of MMp-9.

Induction of MMP-9 in the endotoxin treated mice:

Four BALB/C mice were injected with 18 mg galactosamine with or without endotoxin i.p. The mice were bled (100–200 μl from tail vein) before endotoxin treatment. At 10–11 h. after endotoxin treatment, the mice became sluggish and the mice were bled again. The sera were collected and analyzed by zymogram which demonstrated an increase in the serum level of MMP-9 (Molecular weight 92 Kd) after endotoxin treatment (FIG. 9).

EXAMPLE 6

Induction of MMP-9 in the E. coli treated mice:

Zymogram analysis of serum from mice before and after E. coli(086a:61K) treatment was then effected. Three BALB/c mice (female, 10–12 weeks old, 18–20 g) were given E. coli i.p. and the serum was collected immediately before they died. The sera from mice without E. coli treatment were also collected as negative controls. Lanes 1–10 are the sera (1 μl/lane) from mice without E. coli treatment; lanes 12–14 are the sera from mice after E. coli treatment. These results are shown in FIG. 10.

EXAMPLE 7

This example shows the effect of raxone on septic shock induced by i.p. injection of endotoxin from Salmonella abortus equi.

Effect of razoxane in preventing death due to endotoxin-induced septic shock. Twelve BALB/c mice (female, 10–12 weeks old, 18–20 g) were injected i.p. with endotoxin (Salmonella abortus equi) twice at time zero (70 μg/mouse) and 48 h (30 μg/mouse). Razoxane (2 mg/mouse, in 1% sodium carboxymethyl cellulose) was given i.p. three times, i.e., 1 h. before, 9 h. and 20 h. after injection of initial dose of endotoxin. Another twelve mice, injected with endotoxin as above, were treated with buffer solution (1 % sodium carboxymethyl cellulose) as negative controls. The results of this experiment are shown in FIG. 11. It can be seen therein that the majority of control mice were dead within 50 hours of the initial endotoxin administration. In contrast, approximately 80% of the razoxane treated mice were still alive after 50 hours. Moreover, about 60% of the razoxane treated mice were still alive 100 hours after endotoxin administration, and recovered later on.

These results indicate that bisdioxinpiperazines such as razoxane comprise utility in the treatment of septic shock.

EXAMPLE 8

The example shows the effect of compound 80 (3aα, 5β, 6α, 7aβ)-4,4'-(hexahydro-2,2-dimethyl-1,3-benzodioxole-5, 6-diyl)bis(2,6-piperazinedione) (80) on septic shock.

Effect of Compound 80 in preventing death due to endotoxin-induced septic shock. Twenty BALB/c mice (female, 10–12 weeks old, 18–20 g) were injected i.p. with endotoxin (Salmonella abortus equi, 100 μg/mouse). Compound 80 (0.33 mg/mouse) was given i.p. to 10 mice three times, i.e., 1 hour before, 9 hours and 20 hours after injection of endotoxin. The other 10 mice were injected with diluents as negative controls. The number of the mice survived at different periods to time after endotoxin injection were recorded. (P<0.0002). These results are depicted in FIG. 12.

TABLE 2

Effect of TIMP-2, razoxane and Compound 80 on shock caused by TNF and endotoxin in mouse model:

| Treatment | Survival/Total Ratio | | |
|---|---|---|---|
| | after 24 h | after 48 h | after 72 h |
| galactosamine + TNF | 0/2 | — | — |
| galactosamine + TNF + TIMP-2 | 1/1 | 1/1 | 1/1 |
| galactosamine + endotoxin$_1$ | 2/22 | 0/22 | — |
| galactosamine + endotoxin$_1$ + TIMP-2 | 5/10 | 4/10 | 3/10 |
| galactosamine + endotoxin$_1$ & razoxane | 2/10 | 2/10 | 2/10 |
| endotoxin$_2$ | 10/22 | 3/22 | 0/22 |
| endotoxin$_2$ and razoxane | 10/12 | 9/12 | 7/12 |
| endotoxin$_2$ and Compound 80 | 10/10 | 8/10 | 6/10 |

Note:
Endotoxin$_1$ = lipopolysaccharide from *E. coli* 026:B6
Endotoxin$_2$ = lipopolysaccharide from Salmonella abortus equi

EXAMPLE 9

This example generally describes in vitro methods for evaluating the collagenase inhibitory activity of candidate bis(dioxopiperazine) compounds.

In Vitro Invasion Assay

Razoxane, various bis(hydroxylated)(2,6-dioxopiperazine)s, and various hydrophobic analogs were tested in an in vitro assay for inhibition of tumor cell penetration of a reconstituted basement membrane, matrigel, isolated from the Englegbreth-Holm-Swarm (EHS) tumor (disclosed in Kleinman et al., *Biochem.* (1982), 24, 6188–6193) first described by Albini et al, *Cancer Res.* (1987) 47, 3234–3245. An 8 μm pore filter coated with matrigel separates a lower compartment containing a chemoattractant and an upper compartment containing the cells and test compound. In particular, the following compounds were tested: razoxane, (1α, 2α, 4α, 5α)-4,4'-(4,5-dihydroxy-1,2-cyclohexanediyl)bis(2,6-piperazinedione); (1α, 2α, 4β, 5β)-4,4'-(4,5-dihydroxy-1,2-cyclohexanediyl) bis(2,6-piperazinedione); (1β, 2α,4α,5α)-4,4'-(4,5-dihydroxy-1,2-cyclohexanediyl)bis(2,6-piperazinedione); (1β, 2α, 4α,5β)-4,4'-(4,5-dihydroxy-1,2-cyclohexanediyl) bis(2,6piperazinedione); (1α, 2β, 4α,5β)-4,4'-(4,5-dihydroxy-1,2cyclohexanediyl)bis(2,6-piperazinedione); N,N'-cyclohexane-1,2-diylbis[N(2-ethoxy-2-oxoethyl)] glycine; N,N'-4-cyclohexene-1,2-diylbis[N-(2-ethoxy-2-oxoethyl)-glycine ester; (3aα, 5β, 6β, 7aα)-4,4'-(hexahydro-2,2-dimethyl1,3-benzodioxole-5,6-diyl)bis(2,6-piperazinedione); (3aα, 5α, 6α, 7aα)-4,4'-(hexahydro-2,2-dimethyl-1,3-benzodioxole-5,6-diyl)bis(2,6-piperazinedione); (3aα, 5α, 6β, 7aα)-4,4'-(hexahydro-2,2-dimethyl-1,3-benzodioxole-5,6-diyl)bis-2,6-piperazinedione); (3aα, 5β, 6α, 7aβ)-4,4'-(hexahydro-2,2dimethyl-1,3-benzodioxole-5,6-diyl)bis(2,6-piperazinedione); and (3aα, 5α, 6β, 7aβ)-4,4'-(hexahydro-2,2-dimethyl-1,3-benzodioxole-5,6-diyl) bis(2,6piperazinedione). Metastatic cells are able to degrade the basement membrane protein barrier and migrate through the pores of the filter whereas non-metastatic cells remain on the upper surface. The cells that pass to the under side of the filter are then counted under a microscope. The ability of tumor cells to penetrate matrigel has been shown to depend on the degradation of collagen type IV in the matrigel by type IV collagenase (Reich et al., *Cancer Res.* (1988) 48, 3307–3312). Variations of this assay have been used to correlate this in vitro invasion with metastatic potential in vivo (Albini et al. (Id.); Hendrix et al. *Cancer Letters* (1987); 38, 127–247; Repesh L. A., *Invasion Metastasis* (1989) 9, 192–208 to select for more highly invasive cells (Teranova et al., *Proc. Nat. Acad. Sci.,* (1986), 83, 465, 464; Tullberg et al., *Invasion Metastasis,* (1989), 9, 13–26; Sefer et al., *Biotechniques,* (1990), 9, 324–331), and to test compounds for inhibition (Nakajima et al., *Cancer Res.* (1989), 49, 1698–1756).

This method has been improved to increase the number of assays which may be performed and analyzed per day. In particular, such improvement comprises the use of disposable Transwells (Costar) units described by Repesh et al., *Invasion Metastasis,* (1989), 9, 192–208, which consist of an 8 μm pore filter attached to an insert that fits in a 24 well culture plate. Matrigel concentration is titrated from zero to complete inhibition of motility of each invasive cell line used in the assay and for each batch of matrigel. The matrigel concentration which yields 50% or greater inhibition of motility in a 6 hr assay (usually from 15 to 50 μg of protein per filter) is chosen for determination of invasion. Motility of cells through the 8 μm filters is not by passive diffusion since the pore size is smaller than the cells, and is determined in the same chamber in the absence of matrigel. Motility is stimulated two-fold by the presence of fibroblast conditioned medium (3T3 cells) as a chemoattractant (data not shown). The cell lines used are HT-1080, a human fibrosarcoma, and MDA-MB-231, a human breast carcinoma (both available from the American Type Tissue Culture). These cell lines express both the 72 kD and the 92 kD collagenase type IV as determined by zymography (data not shown).

Compounds to be tested are dissolved in DMSO and are added in a maximum of 1% DMSO (determined not to significantly affect motility or invasion of HT-1080 and MDA-MB-231 cells, data not shown). For inhibition studies, 5×10$^5$ cells are plated in 200 μl of DMEM+0.1% BSA+the inhibitor (or appropriate solvent control) into the upper chamber of the Transwell. To the bottom of the plate, 800 μl of 3T3 conditioned medium containing DMEM+2% NuSerum (Collaborative Research Inc.) is added in contact with the underside of the Transwell filter. For inhibition of invasion, the filters are pre-coated with matrigel at the appropriate concentration. The assay is effected at 37° C. for 6 hours. At the end of the assay the entire filter is stained and fixed in 0.5% crystal violet in 20% MeOH for 15 min. The filters are then rinsed in water and the non-invasive cells remaining on the upper surface of the filters are wiped off with a cotton swab. Invasive cells found on the under side of the filter are quantitated by solubilizing the stain in 10% acetic acid 20% MeOH and the absorbance read at 595 nm. Data comparing cell number was determined by counting cells on the bottom of the filter is directly proportional to absorbance at 595 nm (data not shown).

This assay was validated using TIMP-2, the natural inhibitor of the 72 kD collagenase type IV (Stetler- Stevenson et al., *J. Biol. Chem.*, (1989) 264, 1353–1356). TIMP-2 inhibited the in vitro invasion of HT-1080 cells in the subject assay in a dose dependent manner with an IC50 of 13 μM (FIG. 13) without effecting the motility of the cells (data not shown). Two bis(dioxopiperazine)s, specifically (3aα, 5α, 6β, 7aα)-4,4'-hexahydro-2,2dimethyl-1,3-benzodioxole-5,6-diyl) bis-2,6-piperazinedione (78) and (3aα, 5β, 6α, 7aβ)-4,4'-hexahydro-2,2-dimethyl-1,3-benzodioxole-5,6-diyl) bis-2,6-piperazinedione (80), were found in this preliminary screen to inhibit invasion of both HT-1080 and MDA-MB-231 cells without inhibiting cell motility. FIG. 14 shows a dose response of (3aα, 5β, 6α,7aβ)-4,4'-hexahydro-2,2-dimethyl-1,3-benzodioxole-5, 6-diyl) bis-2,6-piperazinedione on the invasion of HT-1080 cells with a maximum of 62% inhibition at 125 μM. (3aα, 5α, 6β, 7aα)-4,4'-hexahydro-2,2-dimethyl-1,3-benzodioxole-5,6-diyl) bis-2,6-piperazinedione also inhibited invasion with a maximum of 25% inhibition at 290 μM. Consistent inhibition of invasion without effect on motility could not be demonstrated for razoxane from 250 μM to 1 mM.

Biochemical Assays of Basement Membrane Degradation

Type IV collagenases are highly efficient in digesting gelatin. Inhibition of the gelatinase activity of human recombinant collagenase type IV was used as an initial assay for testing the bis(dioxopiperazine)s. The recombinant 72 kD collagenase IV used in the gelatinase assays was made in *E. coli* from a cDNA insert obtained from Dr. William Stetler-Stevenson (NCI). The protein runs at 72 kD on SDS-PAGE, has gelatinolytic activity in zymogram, is activated by pAPMA, is precipitated by a monoclonal anti-peptide antibody to the pro-region of the 72 kD enzyme, and is inhibited by TIMP-2. Rat tail $^3$H-collagen I (Dupont-NEN) is denatured to become gelatin by heating at 60° C. for 20 min. *E. coli* recombinant human 72 kD collagenase type IV is activated by incubation with 1 mM pAPMA for 1 hr. at 37° C. 100 ng of activated enzyme is added to each tube containing 50 mM Tris-HCl pH 7.5, 5 mM $CaCl_2$ and 0.005% Brij-35 and pre-incubated with inhibitor or solvent control for 4 hrs. at 37° C. in a total of 25 μl. 10,000 cpm of $^3$H-gelatin substrate in 30 μl is added (final volume of 55 μl per sample) and the reaction mixture is incubated at 37° C. for 2 to 16 hrs. Undigested material is then precipitated with a solution of 10% trichloroacetic acid (TCA)/1% tannic acid (TA) and 0.5% BSA as a carrier for 10 min. on ice and then centrifuged at 18,000×g for 10 min. at 4° C. Enzyme activity is calculated from the radioactivity in the supernatant and activity of the compounds expressed as percent solvent control. FIG. 15 shows the dose dependent inhibition of collagenase type IV by the above-noted bis(dioxopiperazine)s shown to comprise collagenase inhibiting activity under conditions where TIMP-2 yielded 95% enzyme inhibition. (3aα, 5β, 6α, 7aβ)-4,4'-hexahydro-2,2-dimethyl-1,3-benzodioxole-5,6-diyl) bis(2, 6piperazinedione) (80) and (3aα, 50α, 6β, 7aα)-4,4'-hexahydro-2,2-dimethyl1,3-benzodioxole-5,6-diyl) bis(2,6-piperazinedione) (78) have $IC_{50}$'s of 8 and 45 μm respectively. It is of interest that these two analogs respectively possess the sterically least hindered quasi-diequatorial and diequatorial dioxopiperazine functionalities.

Biochemical Assays of Basement Membrane Degradation

All compounds are tested for inhibition of gelatinase activity and those that inhibit will be tested for their ability to degrade collagen and in a zymography assay. In addition to the effect on pAPMA activated enzyme the effect of the compounds on activation of the enzyme by pAPMA by preincubating the enzyme with inhibitor or solvent control for 1–4 hrs. before addition of the activator is determined. Kinetics of this assay in the presence of DMSO will be determined and $IC_{50}$'s compared for each candidate compound.

Degradation of $^3$H Gelation

Preferably, degradation of 3H-gelatin will be determined because it is known that type IV collagenases are highly efficient in digesting gelatin. Rat tail $^3$H-collagen 1 (Dupont-NEN) is denatured to become gelatin by heating at 60° C. for 20 min. The assay is performed as described supra.

Collagen Degradation

Collagen degradation will be determined using $^3$H-collagen IV. A stock solution of $^3$H-collagen IV (Dupont-New England Nuclear) is diluted 1:50 with a 1 mg/ml solution of pepsinized collagen IV isolated from the EHS tumor as previously described in (Kleinman et al., *Biochem.*, (1982), 24, 6188–6193). The assay is identical to degradation of $^3$H-gelatin described supra except that 10 μl of diluted $^3$H-collagen IV is used as the substrate. This assay is specific for the 72 kD and 92 kD type IV collagenases.

Zymographic Assays

Zymographic assays are effected as follows. Culture media supernatants from several cell lines which produce a variety of metalloproteinases will be run on SDS-PAGE gels containing gelatin (zymogram) which show the pro and active forms of 92 and 72 kD type IV collagenases. 10% polyacrylamide gels are prepared containing 0.5 mg/ml gelatin and samples are mixed in 4× X sample buffer without heating or reducing agents. After electrophoresis, the gels are incubated in 2.5% Triton-X100 for 30 min. to remove the SDS, and then incubated for 16 hrs. in 50 mM Tris-HCL pH 7.5, 5 mM $CaCl_2$ and 0.005% Brij-35 at 37° C. (in the presence or absence of inhibitor), and then stained with 0.5% Coomassie Blue in 10% MeOH 5% acetic acid for 30 min. After destaining the gels in 10% MeOH 5% acetic acid, bands of gelatinolytic activity are detected as cleared bands against the blue-stained gelatin background.

Invasive Characteristics of the Cell Lines in Vitro

The ability of razoxane and other bis(dioxopiperazine)s to inhibit the in vitro invasion assay will be determined as described supra. All compounds will be tested in both cell lines at the maximum non-toxic dose. Toxicity of the compound initially is determined by incubating several log doses of the compound and solvent controls for 6 hr (the length of the invasion assay) and 24 hr in serum-free medium. Cell number is determined by comparing the absorbance of crystal violet with controls, and membrane damage and cell death determined by trypan blue dye exclusion. Candidate bisdioxopiperazine compounds will be tested for their effect on cell motility and invasion through basement membrane. Compounds that effect motility and invasion will be further tested for dose response. Compounds that inhibit motility will be closely evaluated to determine if this is a specific effect on motility or a general toxic response.

The crystal violet staining method of quantitation described supra is much more rapid than counting cells in a microscope field and is very reproducible. A possible problem with this method of quantitation is that dye uptake may be effected by the test compound. Accordingly, determinations will be made to determine visually if the cells are stained evenly and to see if absorbance is consistent. All compounds shown to be effective in the assay will be tested for their effect on dye uptake by comparing cell counts with absorbance.

Experiments to further evaluate positive compounds in the in vitro assay will involve three initial strategies: 1) The effect of pretreating the cells with the test compound will be evaluated. If the effect of the compound is in blocking production of proteases then pretreating the cells for 1 to 3 days should increase the inhibition detected in the invasion assay. 2) Accordingly, experiments will be conducted to determine if inhibition by these compounds can be blocked. If the mechanism of action is based on the metal binding capability of the compounds, addition of excess ions may block drug action. 3) Additionally, experiments will also be conducted to determine if these compounds act synergistically with other inhibitors of in vitro invasion such as TIMP-2 or monoclonal antibodies to metalloproteinases.

Cell Interaction with the Basement Membrane

Friedman et al., *Invasion and Metastasis,* (1990), 10, pp. 208–224 have shown that cell adhesion and migration are as important as collagenase type IV activity in determining the in vitro invasiveness of cells. Accordingly, experiments will be conducted to test the effects of specific bisdioxopiperazines on attachment to individual components of basement membrane. For attachment assays, tissue culture dishes (35 mm) are coated with 1–100 µg of either laminin, fibronectin, collagen IV, or matrigel diluted in 1 ml of phosphate-buffered saline (PBS) for 1 hr. at 37° C., followed by three washes with PBS. The dishes are then incubated for 1 hr. at 37° C. with DMEM containing 2% BSA and then washed 5 times with DMEM containing 0.1% BSA. Cells suspended in DMEM containing 0.1% BSA (with and without cycloheximide at 25 µg/ml to block cell synthesis of attachment factors) with the inhibitor or appropriate solvent control are seeded at $2 \times 10^5$ cells per dish. After 1 hr. of incubation at 37° C. the unattached cells are removed by gentle washing and the firmly attached cells disassociated with trypsin-EDTA and counted with a Coulter Counter. To examine cell spreading, cells are attached to the substrate as above then fixed and stained with Diff-Quick (American Scientific Products). The effect of pretreating the cells for 1–3 days with specific bisdioxopiperazines will also be determined.

Effects on Synthesis of Proteases and Endogenous Inhibitors

The data contained herein indicates that some bisdioxopiperazine compounds directly inhibit metalloprotease enzyme activity which is consistent with the proposed mechanism of action by some research groups. Further experiments will be conducted to evaluate the effect of bisdioxopiperazines on the production of matrix metalloproteases and TIMP's by cell lines using zymograms and western and northern blotting.

Zymograms

Zymograms will be effected as follows. The gelatinolytic activity of collagenases from bis(dioxopiperazine) treated cells will be determined in SDS-PAGE gels containing gelatin (zymogram) which show the pro and active forms of 92 and 72 kD type IV collagenases.

Western Blotting

Western blotting will be effected as follows. Bisdioxopiperazine-treated and control untreated cell cultures will be lysed in 25 mM Tris-HCl pH 7.5 containing 4 mM EDTA, 100 mM NaCl and 1% NP-40 by sonication. Protein concentration will be determined using the BCA reagent kit (Pierce). Appropriate protein concentrations will be added to 4× sample buffer, boiled for 3 min., and run on nitrocellulose sheets and specific proteases and TIMP's will be detected using antisera or monoclonal antibodies. Polyclonal antisera to TIMP and TIMP-2, interstitial collagenase, 92 kD collagenase type IV, stromelysin I and II, and PUMP-1, and monoclonal antibody to 72 kD collagenase type IV will be used as probes.

Northern Blotting

Northern blotting will be effected as follows. RNA will be extracted from bisdioxopiperazine-treated and control untreated cell cultures using guanidine thiocyanate and purified using cesium chloride density gradient centrifugation. Total RNA will be separated on 1% agarose gels containing formaldehyde and transferred to nitrocellulose. Specific MRNA will be detected using cloned probes made radioactive using nick translation with $^{32}p$ dCTP (Sanbrook et al., *Molecular Cloning: A Laboratory Manual,* (1989), 7.23–7.52). Probes will include, e.g., cDNA for TIMP-2, 72 kD and 92 kD collagenase type IV, and other metalloproteases including interstitial collagenase, stromelysin I and II, and PUMP-1.

Compounds found to be active in the described in vitro assays will then be tested in animal models of metastasis and compared to the activity of the parent compound ICRF-159. This will enable the identification of functions which increase anti-metastatic activity and should further facilitate the rational design of novel bisdioxopiperazine therapeutics.

Histological Evaluation of Tumor Vasculature

We will evaluate the primary tumors and subsequent metastases from the animal models for a variety of parameters pertaining to both the tumor cells and microvasculature. Animals are sacrificed by cervical dislocation at various times and the primary tumors (with surrounding tissue), lungs, liver and internal metastases will be removed and weighed. The primary tumor will also be measured in three dimensions. The tissues will be fixed in 10% buffered formalin for 24 hours for paraffin embedding. Metastases are quantitated by counting the number observed on H & E stained sections. Tumors will be characterized for cellular atypia, architecture and necrosis. A specific search will be made to identify vascular invasion within both primary and metastatic lesions. The blood vessels of the tumor and surrounding tissue will be assessed for evidence of perivascular lymphocyte, cuffing, caliber, number and intactness. The vascular pattern will be characterized by immunohistochemical staining with an endothelial cell specific marker, polyclonal antibody to human von Willebrand Factor (Dakopatts). Average vascular caliber will be estimated for central and peripheral vessels, and compared to vessels in adjacent normal tissue. Specific search will be made for gaps in the endothelial cell lining.

The vascular basement membrane will be assessed by staining with monoclonal antibody to human collagen type IV (Dakopatts). Specific search will be made for gaps in vessel basement membrane and the size and number of these gaps will be scored. Finally, the tumors will be evaluated for the level of collagenase type IV expression by staining with a mouse monoclonal anti-human collagenase type IV antibody (Oncologix, Inc.). The percentage of cells staining strongly, weakly, or not at all will be scored at central, peripheral and perivascular locations. Correlations will be sought between collagenase type IV expression, vascular integrity, and number of metastases found in the untreated animals.

Endothelial Cell Proliferation

Razoxane and bis(dioxopiperazine)s will be tested for their effects on endothelial cell proliferation. For these studies two different types of endothelial cells will be used: cloned populations of adult bovine aortic endothelial (ABAE) and bovine adrenal capillary endothelial cells. Cells will be obtained and cultured. In particular, endothelial cells will be seeded in 35 mm plastic tissue culture dishes ($3 \times 10^3$ cells/dish) in DMEM (low glucose) supplemented with 10% FCS. Under these conditions, endothelial cells can proliferate only if bFGF (basic fibroblast growth factor) at concentrations of 50–100 ng/ml is added every other day. In the absence of bFGF, cell growth is almost absent. Potential inhibitors of collagenases tested as described in biochemical assays will be added in various concentrations to proliferating endothelial cells. Determinations of cell growth will be performed by counting the cells electronically (Coulter counter) after trypsinization or by measuring DNA synthesis by $^3$H-thymidine incorporation. Trypan blue exclusion assays will be performed simultaneously with these assays to detect any possible effect on cell viability by these compounds.

Angiogenesis assays. The effects of razoxane and bis (dioxopiperazine)s on the formation of capillaries by endothelial cells will be investigated in two different systems described below:

(1) Tube assays on matrigel. Matrigel (250 µl of 25 mg/ml) at 4° C. is used to coat each well of a 24 well plate and allowed to polymerize at 37° C. for a minimum of 30 min. 50,000 ABAE cells/well are added with inhibitor or solvent control and the plate is incubated overnight at 37° C. in an humidified chamber with 5% $CO_2$. The medium is then carefully removed and the cells methanol-fixed and stained with a modified Geimsa blue stain. Tube formation is examined visually on a Zeiss 1 M light microscope equipped with an Olympus camera. In some experiments, the medium will be removed and analyzed in a Coulter counter to determined the number of floating cells.

(2) The Chick Chorioallantoic Assay (CAM). Fertilized four day old chicken eggs are cracked open by peeling the shell away from the air sac region. The contents of the egg are poured out into 8 oz. paper cups in which Saran plastic wrap has been draped across to support the yolk, embryo and CAM. The eggs in the cup are incubated at 37° C. in a humidified chamber over a period of 3 days. The CAM usually floats to the top and spreads across the embryo and yolk. From the embryo center, four sets of vascular branches are present, and identified as north, south, east, and west vessels of the chick. The single unbranched northern vessel near the head of the embryo is used to test the compounds. After 24 hours of incubation in the cups, either compound or solvent control is added to the surface of the CAM near the central portion of the vessel. Photographs are taken at 18 and 48 hours later with a Nikon camera equipped with a Macro lens.

In Vivo Models of Metastasis

Razoxane has been shown to be an anti-metastatic agent in numerous animal models of metastasis. Therefore, those bis(dioxopiperazines) found to exhibit in vitro anti-collagenase activity will be evaluated in available animal models of metastasis. Preferably, razoxane and selected bis(dioxopiperazine)s will be tested in the LS-MET model of a metastatic human colon carcinoma.

This is a model for spontaneous metastasis currently under development. This metastatic model utilizes a human colon carcinoma cell line which readily forms distant site metastasis following establishment of a subcutaneous (s.c.) primary tumor. The parenteral line (LS-MET-1) was established from a rare hepatic metastasis after implantation of LS-174T human colon carcinoma in the median lobe of the liver. The metastatic cell line (LS-MET-2) was established in a similar manner from LS-MET-1 cells. Nude mice received s.c. injections of LS-MET-1 and the LS-MET-2 cell line and primary tumors$\leq 1$ cm were surgically removed at day 12. None of the mice receiving the LS-MET-1 line developed metastases by week 12, but, 3/5 mice receiving the LS-MET-2 cell line had liver and/or lung metastases by week 5. The LS-MET-2 line grown continuously as a s.c. tumor is invasive and lethal in less than 20 days.

The LS-MET-5 line is a related cell line which forms metastases of lung, lymph, brown fat, kidneys, adrenals, brain, and peritoneal and thoracic cavity seeding after intravenous injection. This model reflects the end stages of metastasis, i.e., that of extravasation, implantation, and growth at distant sites. Mice develop multiple metastases as early as 21 days after injection of $1 \times 10^6$ cells with a mean survival of 40 days.

Advantages of this model over other models described in the literature are (1) these cells are a human carcinoma. It is well documented that primary and secondary metabolism of compounds can vary considerably between human and rodent cells. Predictably most metabolism would occur by the mouse host but differences within the tumor cells could play an important role in drug action. (2) Animal survival would be a rapid quantitative endpoint. (3) S.c. injection and subsequent tumor removal is easier than many models that require complex surgical procedures to implant cells within the host organs. (4) Agents would only have to be given while the primary tumor was present to test for anti-metastatic activity and thus experiments would be compound sparing.

However, as noted, the described LS-MET model is still under development. In the event that the model is not established as quantitative and reproducible, we will use a combination of the Lewis lung spontaneous mouse model and tail vein injection of human melanoma. The most widely used model of metastases is the Lewis lung carcinoma of the mouse (3LL). After establishment of a s.c. primary tumor, the cells metastasize to the lungs of the host mouse. Tumor sensitivity to clinically active antineoplastic drugs is similar to many solid tumors in man. Another type of model which only evaluates compounds effects on the end stages of the metastatic cascade is the tail vein injection of tumor cells which subsequently form colonies in the lungs. We propose to use the human melanoma cell line, A2058, which forms lung colonies after tail vein injection, to evaluate inhibition of extravasation and implantation into distant sites.

Alternatively, candidate bisdioxopiperazine compounds may be tested in the OVCAR-3 model of human ovarian carcinoma in the nude mouse as developed by Hamilton et al., *Cancer Research* (1984), 44, 5286–5290. In this model ovarian carcinoma cells attach to and invade the peritoneal cavity.

EXAMPLE 10

TIMP-2 TREATMENT OF LS-MET-5 i.v. METASTASES

Test 1

Experimental Design:

Vaccinia recombinant human TIMP-2 was diluted to 4.1 mg/ml in acetate buffer, filter sterilized using 0.22 µm spinex filters, and 224 µl added to Alzet mini osmotic pumps (series 2001—at least 7 day delivery of 1 µl/hr). The pumps have a 95% expected delivery for a maximum of 870 µg of TIMP-2/mouse over 8 days. Control pumps contained the acetate buffered vehicle alone.

Females HSD nu/nu mice approximately 6 weeks old with a mean weight of 20 grams were used. The pumps were inserted in the s.c. dorsal region using standard surgical procedures. Five hours after pump implantation, the mice received $1 \times 10^6$ LS-MET-5 human colon carcinoma cells via a lateral tail vein. After 8 days the pumps were surgically removed and volume remaining in the pumps was determined. TIMP-2 was not completely delivered in two of the mice (180 and 170) with 50 and 30 µl remaining.

Results:

Superficial metastases were observed beginning at day 22 in the control group. Mice were sacrificed on day 27. Control mice had significant disseminated disease. Of the five TIMP-2 treated mice, only the two which had incomplete delivery of the pump had visible disseminated disease. An additional mouse had microscopic lesions observed on Hematoxylin and Eosin stained slides, and two mice had no histological evidence of micro metastases. The summary of the results is set forth in Table 3.

Test 2

Experimental Design:

Vaccinia recombinant human TIMP-2 was diluted to 5.7 mg/ml in acetate buffer, filter sterilized using 0.22 µm spinex filters, and 235 µl added to Alzet mini osmotic pumps (series 2001—at least 7 day delivery of 1 µl/hr). The pumps have a 95% expected delivery for a maximum of 1.27 mg of TIMP-2/mouse over 9 days. Control pumps contained the acetate buffer vehicle alone.

Females HSD nu/nu mice approximately 6 weeks old with a mean weight of 20 gr were used. The pumps were primed in 0.9% sterile saline for 4 hours and inserted in the s.c. dorsal region using standard surgical procedures. Twenty hours after pump implantation, the mice received $1 \times 10^6$ LS-MET-5 human colon carcinoma cells via a lateral tail vein. After 11 days the pumps were surgically removed and volume no significant volume remained in any pump.

Results:

Metastasis

Superficial metastases were observed beginning at day 22 in the control group. By day 25 the different between the control and TIMP-2-treated mice was dramatic. Sacrifice was scheduled for day 32. On day 28, 2 of the TIMP-2 mice (240 and 255) exhibited difficulty breathing and were sacrificed. Remaining mice were sacrificed on day 32.

Although the TIMP-2 mice had metastatic disease there may be a shift in the pattern of metastasis in these mice. There appeared to be a lower percentage of the total metastatic burden in the superficial metastases in the TIMP-2 mice. TIMP-2 from the pump would be delivered in the s.c. space and then taken up by the microvasculature. These results are set forth in Table 4.

TABLE 3

SUMMARY OF OBSERVED METASTASES IN MICE INJECTED I.V. WITH LS-MET-5, CONTROL AND TIMP-2 TREATED

| Mouse | Met Wt. | Dorsal Thoracic | Ventral Cervical | Kidney Adrenal | Abdominal Seeding | Thoracic Cavity | Lung | Thigh | Axillary Lymph |
|---|---|---|---|---|---|---|---|---|---|
| Control | | | | | | | | | |
| 177 | 0.25 | +++ | – | – | +++ | +++ | – | – | – |
| 179 | 1.6 | +++ | +++ | +++ | +++ | +++ | – | – | – |
| 185 | 2.0 | +++ | +++ | +++ | +++ | +++ | – | – | – |
| 192 | 1.0 | +++ | +++ | +++ | – | +++ | – | – | – |
| TIMP-2 | | | | | | | | | |
| 170 | 1.7 | +++ | +++ | +++ | +++ | +++ | – | +++ | +++ |
| 180 | 0.91 | +++ | +++ | – | +++ | +++ | + | – | – |
| 182 | — | ++ | – | – | + | – | + | – | – |
| 190 | — | – | – | – | – | – | – | – | – |
| 174 | — | – | – | – | – | – | – | – | – |

+++ gross metastases confirmed by histology
++ macro metastases observed on H&E slide
+ micro metastases observed on H&E slide only under a microscope
– no observed metastases

TABLE 4

Effect of TIMP-2 on Mice Injected i.v. with LS-MET-5

| | Total Met Weight | Dorsal Thoracic | Salivary | Axillary Lymph | Inguinal Lymph | Thigh | Head | Foreleg | Thoracic Cavity | Lung | Kidney | Abdominal Seeding | Spine | Heart | Pancreas |
|---|---|---|---|---|---|---|---|---|---|---|---|---|---|---|---|
| Control 246 | 4.73 | 1.23 | 1.25 | 1.35 | — | — | — | — | **** | — | 0.56 | 0.34 | * | — | * |
| 247 | 3.03 | 1.44 | 0.58 | 0.65 | — | — | — | — | ** | * | 0.17 | 0.19 | — | — | — |
| 243 | 2.76 | 0.94 | 0.13 | 0.16 | — | — | 0.03 | — | 1.3 | — | 0.11 | 0.09 | * | — | — |
| 248 | 1.84 | 0.45 | 0.56 | 0.38 | — | 0.22 | — | * | **** | — | ** | 0.22 | — | — | — |
| 244 | 0.55 | 0.1 | — | — | — | 0.27 | 0.05 | — | ** | — | — | 0.13 | — | — | — |
| TIMP-2 255 | 2.33 | 0.58 | 0.17 | 0.3 | 0.05 | — | — | — | 0.94 | * | ** | ** | — | * | — |
| 240 | 2.33 | ** | 0.36 | 0.48 | — | — | — | 0.33 | 0.95 | * | 0.21 | ** | — | — | — |
| 239 | ** | ** | — | ** | — | — | — | — | ** | * | ** | ** | — | — | — |

\* Microscopic lesion
\*\* Small macroscopic lesion observed at necropsy, too small to weight or unable to free from surrounding tissue.
\*\*\* Large lesions unable to free from surrounding tissue to weigh.

EXAMPLE 11

This example compares using a gelatinase assay and the collagenase inhibitory activity of various compounds, namely EDTA, razoxane and compound 80. ( (3aα, 5α, 6β, 7aβ)-4,4'-(hexahydro-2,2-dimethyl-1,3benzodioxole-5,6-diyl)bis(2,6-piperazinedione)).

NET-660 Collagen (Rat Type I), N-[Propionate-2-3-$^3$H] Propionylated (NEN Dupont) with a specific activity of 0.4 mCi/mg, rat type I Collagen (Sigma), P-aminophenylmercuric acetate, APMA (Sigma), recombinant human 72 kD type IV collagenase (Oncologix) with a specific activity of at least 1000 μg collagen digested/hour/μg enzyme, collagenase buffer (50 mM Tris-HCl, 5 mM CaCl$_2$, 200 mM NaCl, 0.02% Brij-35, pH 7.6), bovine serum albumin (BSA), 250 mM EDTA, and 10% TCA+0.7% tannic acid. The substrate is prepared by mixing the $^3$H collagen with the cold collagen at a 2/3 ratio and diluting in the collagenase buffer. The final assay concentration of the $^3$H collagen is 1% or between 20,000 to 40,000 cpm. Inhibitors are prepared just prior to use by dissolving in DMSO (final assay concentration<1%) or collagenase buffer.

The 72 kD collagenase enzyme is activated with 0.5 mM APMA for 30 min. at 37° C. and 10 ng of enzyme per assay is used. Inhibitors are preincubated with activated enzyme for 2 hours at 37° C. in collagenase buffer. Substrate is then added to enzyme inhibitor mix and the assay is run for 20 min at 37° C. The assay is stopped with 20 mM EDTA and 15% BSA. Undigested substrate is precipitated with the TCA/tannic acid solution and soluble counts are determined in a scintillation counter. Activity of the inhibitors is determined as percent of the appropriate solvent control and the IC$_{50}$'s, or the amount of inhibitor which causes 50% inhibition of the enzyme activity, determined.

IC$_{50}$'s for inhibition of the 72 kD collagenase type IV were shown to be 300 μM for EDTA, 44 μM for Razoxane and 1.8 μM for compound 80 and are depicted in FIG. 16.

EXAMPLE 12

This example evaluates the collagenase inhibitory activity of razoxane and various bis(dioxopiperazines) using the OVCAR-3 cell line.

The OVCAR-3 cell line was chosen as a model to test the hypothesis that razoxane and bis(dioxopiperazines) are collagenase inhibitors since this is a highly invasive human ovarian carcinoma which when grown i.p. in a nude mouse invades the peritoneum and all organs as well as metastasizing to the lungs. Invasion and metastasis is believed to require matrix metalloproteases such as the 72 kD collagenase type IV. Ascites fluid from OVCAR-3 tumor bearing mice have high levels of this enzyme, on average of 1.0±0.3 μg/ml 22 days post implantation of 20 million cells.

In order to determine if razoxane is effective in treatment of the OVCAR-3 human ovarian cancer model in nude mice the following procedure was effected.

Dose and Schedule—Razoxane was suspended in sterile 1% CMC (carboxymethyl cellulose) 0.9% NaCl by sonication in a water bath. Mice received 30 mg/kg drug in 10 μl/g CMC per i.p. dose beginning 24 hours prior to cell implantation. Each mouse received one dose/day i.p. for 5 consecutive days with 2 days of recovery. Treatment continued until mouse death or sacrifice.

OVCAR-3 cells—were received from Dr. Tom Hamilton and are maintained by passage of ascites directly from the mouse. The ascites is harvested from the mouse by rinsing the peritoneal cavity with HBSS, treated briefly with Dispase to dissociate clumps, centrifuged, counted, resuspended in HBSS and 20 million cells injected i.p. per mouse.

Mice—HSD nu/nu female mice 6 weeks old (18–22 g) are weighed, tagged with a metal ear clip, and randomized for treatment or control groups. Mice are weighed daily and the dose of drug or vehicle is calculated.

Visible ascites appears around day 14 with small solid tumors at the sites of injections. The mice swell with hemorrhagic ascites prior to death. At necropsy mice contain massive invasive carcinomatosis obliterating most of the normal organs of the peritoneal cavity with significant metastasis to the lungs. A 25% increase in mean/median survival time with drug treatment is considered significant in this model.

The difference in the survival time between treated and control mice was significant at >33%. The significance of the life table was p=0.0003 by Log-Rank and 0.0005 by Wilcoxon, the results of which are present in FIG. 17.

The treated mouse sacrificed at day 76 did have an increase in weight of 4 gr and visible tumors at the needle sticks, but evidence of regression occurred with a weight drop of 4 g until the mouse looked normal at sacrifice. Histology revealed residual microlesions in the reproductive tract and an isolated non-invasive micro lesion near the stomach.

EXAMPLE 13

This example evaluates the effect of probimane on the survival of mice which have been injected with LS-MET-5 human colon carcinoma cells. In particular, probimane was given at 26 mg/kg in CMC, 1 intraperitoneal dose/day starting 1 day prior to intravenous injection of 1 million LS-MET-5 human colon carcinoma cells, at either 3 or 5 doses per week. During the first week the treated mice experienced a small weight drop and the dosage was decreased to 10.4 mg/kg. The control mice received CMC only at 10 μl/g.

The effect of probimane on survival of said i.v. LS-MET-5 treated mice is set forth in Table 5, and in FIG. 18.

TABLE 5

Effect of Probimane on Survival of LS-MET-5 i.v.

|  | Control | 5×/Week | 3×/Week |
| --- | --- | --- | --- |
| Day of Death | 36 | 43 | 43 |
|  | 37 | 44 | 44 |
|  | 37 | 44 | 45 |
|  | 40 | 46 | 46 |
|  | 40 | 47 | 52 |
|  | 73 | 49 | 62 |
|  |  | 51 | 63 |
|  |  | 52 | 63 |
|  |  | 58 |  |
|  |  | 73 |  |
| Median Survival | 40 | 47 | 47 |
| Median IST |  | 18% | 18% |
| Mean Survival | 43 | 50 | 52 |
| Mean IST |  | 16% | 19% |

Probimane was given at 26 mg/kg in CMC, 1 i.p. dose/day starting 1 day prior to i.v. injection of 1 million LS-MET-5 human colon carcinoma cells, at either 3 or 5 doses/week. During the 1st week the treated mice experienced a small weight drop and the dosage was decreased to 10.4 mg/kg.
Control mice received CMC only at 10 μl/gr.

EXAMPLE 14

This example evaluates whether the effect of probimane on increased survival in the LS-MET-5 human colon carcinoma model in nude mice is reproducible.

Dose and Schedule—was suspended in sterile 1% CMC (carboxymethyl cellulose) 90% NaCl by sonication in a water bath. Mice received 26 mg/Kg of probimane in 10 μl/gr CMC per i.p. dose the first week, but the dose was dropped in 10.4 mg/Kg (⅕th the molar dose of razoxane) during the second week after a weight drop indicated toxicity. Mice received drug 24 hours prior to injection of cells and each mouse received one dose/day i.p. for 5 consecutive days with 2 days of recovery or 3 consecutive days with 4 days of recovery. Treatment continued until mouse death or sacrifice.

LS-MET-5—human colon carcinoma metastatic variant cell line was developed at Oncologix, Inc. The cells are maintained in culture in DMEM+10% FBS and are dissociated for injection with trypsin/versine. The cells are resuspended in HBSS and 1 million cells injected in 100 μl into the lateral tail vein of the mouse.

Mice—HSD nu/nu female mice 6 weeks old (18–22 g) are weighed, tagged with a metal ear clip, and radomized for treatment or control groups. Mice are weighed daily and the dose of drug or vehicle is calculated.

Superficial metastases in the regional lymph nodes, dorsal thoracic brown fact pad, thigh muscle and on the rib cage begin appearing around day 22. Tumor growth is rapid with small metastases quickly coalescing to form a solid collar of metastases around the neck region of the mouse. Necropsy reveals massive invasive internal metastases located throughout the peritoneal and thoracic cavities including massive lung involvement, and in the CNS particularly in the brain itself.

Although we have improved the incidence of mice with metastases by eliminating mice with less than perfect initial i.v. injections, we are still only 90% incidence. The experiment is terminated when the last mouse with evidence of metastases dies. The remaining mice are necropsied for presence of micro-metastases. We have found evidence that cells were indeed injected iv. (cystic lymph nodes and compression injury in the lungs) but whether or not they did not implant in the mice or were sheared during injection is not known.

There was an early difference in the number of superficial metastases between the control and the treated groups that could be determined before the metastases in the control mice coalesced (see Table 6 below).

TABLE 6

Effect of Probimane on LS-MET-5 i.v. Superficial Metastases

| Day | Control | 5×/Week | 3×/Week |
| --- | --- | --- | --- |
| 29 Incidence | 6/9 | 5/11 | 7/11 |
| Mets Mouse | 2.5 | 1.2 | 1.1 |
| 30 Incidence | 7/9 | 10/11 | 7/11 |
| Mets/Mouse | 3.0 | 1.2 | 1.9 |
| 31 Incidence | 8/9 | 11/11 | 7/11 |
| Mets/Mouse | 2.9 | 1.1 | 1.9 |
| 32 Incidence | 8/9 | 11/11 | 7/11 |
| Mets/Mouse | 3.5 | 1.8 | 1.9 |

This difference in the number of metastases per mouse appeared to correlates with increased survival in the Probimane-treated mice. The increase in survival that is considered to be significant is unknown in this model; it is, however, an extremely aggressive model system and colon cancer is very refractive to chemotherapy. Statistical analysis on the survival curves yielded a p=0.002 by Wilcoxon (weights early survival differences more) and 0.2 by the Log-Rank (emphasis on larger survival times).

The mice receiving 5 doses/week did no better than mice receiving 3 doses/week. Probimane-treated mice appeared to die with less tumor burden that the control mice. The condition of the probimane mice was visibly different than the control mice. They were pale and grayish in color, with scruffy coats, and were cold to the touch particularly in the 5 dose/week group. This is consistent with bone marrow suppression (the rate limiting toxicity of razoxane). Since Probimane may be a soluble prodrug of razoxane we have to determine if increased bioavailability is producing increased toxicity at this dose and schedule.

The use of the bis(dioxopiperazine) compounds found to be capable of inhibiting collagenases, in particular type IV collagenases in vitro, will also be tested for their efficacy in the treatment of stroke, cardiac disorders and arthritis and other collagenase related disorders. Compounds found to inhibit collagenase activity in vitro will be tested in available models for these disease conditions. See, e.g., Courten-Myers et al, *Resuscitation,* (1992), 23, 91–100; Smith et al, *Cardiovascular Research,* (1985), 19, 181–186 and Howell et al, *J. Rheumatology,* (1991), 18, 138–142.

It is to be understood, however, that the scope of the present invention is not to be limited to the specific embodiments described above. The invention may be practiced other than as particularly described and still be within the scope of the accompanying claims.

EXAMPLE 15

This example evaluates the effects of immunotoxin administration on serum metalloproteinase levels. A Cynomolgous monkey, given the internal designation Monkey 4847 was injected intravenously with OLX-209, a *Pseudomonas exotoxin* based immunotoxin. The OLX-209 immunotoxin comprises a single chain antibody which specifically binds to erbB-2 fused via an oligopeptide linker to a fragment of *Pseudomonas exotoxin* lacking the binding domain, and further comprising a deletion of amino acids 365–380 of domain II, and a deletion of the last five amino acids of domain III, which are substituted by the tetrapeptide KDEL. After OLX-209 administration, the monkey was bled at 10, 30, 45, 60, 90, 120, 180 and 240 minutes after injection.

One μl of the serum from each bleeding was diluted in 30 μl of the sample buffered solution (without 2-mercaptoethanol) and 15 μl of the mixture were loaded on each lane of a 1% gelatin SDS gel as follows (from left to right): (1) 10, (2) 30, (3) 45, (4) 60, (5) 90, (6) 120, (7) 180, and (8) 240 minutes after OLX-209 injection. The gel was electrophoresed and developed in collagenase buffered solution for 24 hours. The results of this gelatin Zymogram analysis are found in FIG. 19, and clearly demonstrate that serum MMP-9 levels increases demonstrably after OLX-209 immunotoxin administration.

EXAMPLE 16

This example also studies the effect of immunotoxin administration on serum metalloproteinase levels in a Cynomolgous monkey. A monkey designated monkey 4848 was injected intravenously with OLX-209 and bled at 10, 30, 45, 60, 90, 120, 180, 240, 260 and 480 minutes after administration. One μl of the serum from each bleeding was diluted in 30 μl of the sample buffered solution (without 2-mercaptoethanol) and 15 μl of the mixture were loaded on each lane of a 1% gelatin SDS gel as follows (from left to right): (1) 10, (2) 30, (3) 45, (4) 60, (5) 90, (6) 120, (7) 180, and (8) 240, (9) 360, (10) 480 minutes after OLX-209 injection. The gel was electrophoresed and developed in collagenase buffered solution for 24 hours.

The results of this gelatin Zymogram analysis are found in FIG. 20. These results similarly demonstrate that serum MMP-9 levels increased demonstrably after OLX-209 immunotoxin administration.

What is claimed is:

1. A method for treating septic shock comprising administering to a person at risk of developing or having septic shock, a therapeutically effective amount of one or more compounds selected from the group consisting of:

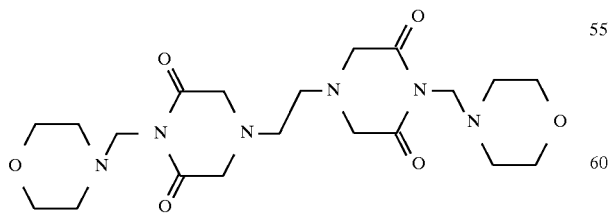

-continued

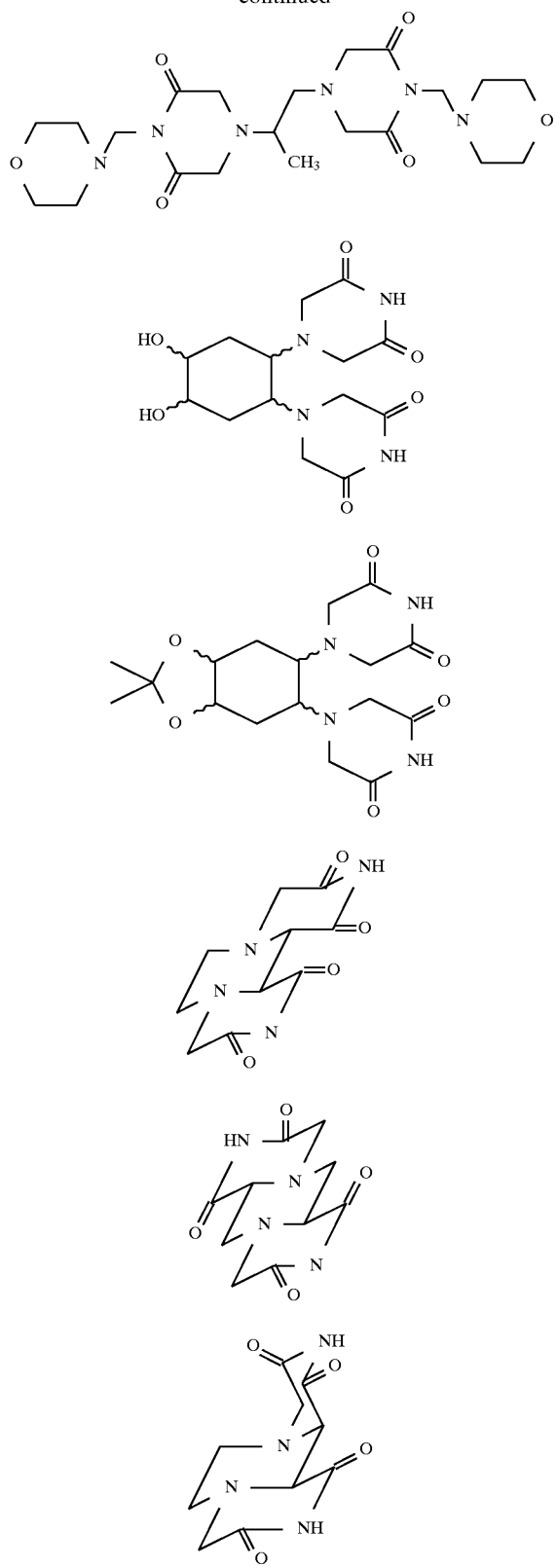

-continued
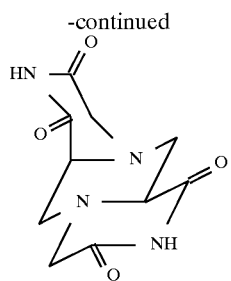
2. The method of claim 1, wherein the therapeutically effective amount ranges from about 0.1 to about 2.0 mg/kg body weight per day.
individual optical, diastereomeric, and geometric isomers thereof, pharmaceutically-suitable salts thereof, and combinations thereof.